US012649734B2

(12) United States Patent
Jha et al.

(10) Patent No.: US 12,649,734 B2
(45) Date of Patent: Jun. 9, 2026

(54) BIOAVAILABLE PROTEIN DISULFIDE ISOMERASE INHIBITORS

(71) Applicant: THE CLEVELAND CLINIC FOUNDATION, Cleveland, OH (US)

(72) Inventors: Babal K. Jha, Cleveland, OH (US); James G. Phillips, Cleveland, OH (US); Frederic J. Reu, Cleveland, OH (US); Metis Hasipek, Cleveland, OH (US); Dale Grabowski, Cleveland, OH (US); Jaroslaw P. Maciejewski, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 575 days.

(21) Appl. No.: 18/023,087

(22) PCT Filed: Aug. 27, 2021

(86) PCT No.: PCT/US2021/047832
§ 371 (c)(1),
(2) Date: Feb. 24, 2023

(87) PCT Pub. No.: WO2022/047086
PCT Pub. Date: Mar. 3, 2022

(65) Prior Publication Data

US 2023/0312552 A1 Oct. 5, 2023

Related U.S. Application Data

(60) Provisional application No. 63/070,855, filed on Aug. 27, 2020.

(51) Int. Cl.
*C07D 417/14* (2006.01)
*A61K 31/427* (2006.01)
*A61P 35/00* (2006.01)

(52) U.S. Cl.
CPC ............ *C07D 417/14* (2013.01); *A61P 35/00* (2018.01)

(58) Field of Classification Search
CPC ... C07D 417/14; C07D 417/06; A61K 31/427
USPC .......................................... 548/183; 514/369
See application file for complete search history.

(56) References Cited

U.S. PATENT DOCUMENTS 9,359,342 B2 * 6/2016 Reu ...................... C07D 495/04
2015/0133514 A1 * 5/2015 Reu ........................ A61K 47/60 514/369
2018/0370912 A1 12/2018 Flaumenhaft et al.

OTHER PUBLICATIONS

Communication pursuant to Article 94 (3) EPC dated Aug. 9, 2025 for Application No. 21 862 774.3-1102, 4 pages.
PCT International Search Report dated Dec. 14, 2021. pp. 1-6.
Canadian Office Action for Corresponding Application Serial No. 3,150,083, Dated Mar. 21, 2023, pp. 1-3.
Extended European search report dated Feb. 8, 2024 for corresponding application No. 21862774.3-1102 / 4203894 PCT/US202104832, 8 pages.
Hasipek Metis et al: "Therapeutic Targeting of Protein Disulfide Isomerase PDIA1 in Multiple Myeloma", CANCERS, vol. 13, No. 11, May 28, 2021 (May 28, 2021), p. 2649, XP093189143, CH ISSN: 2072-6694, DOI: 10.3390/cancers 13112649 * abstract; figure 2B *.

* cited by examiner

*Primary Examiner* — Charanjit Aulakh
(74) *Attorney, Agent, or Firm* — Tarolli, Sundheim, Covell & Tummino LLP

(57) ABSTRACT

Compounds according to formula (I) are described wherein $R^1$ is an amino acid or a modified amino acid linked to the compound through a peptide bond, $R^2$ is selected from CN, $SO_2CH_3$, $NO_2$, $CO_2R^3$, $CONHR^3$, $NH_2$, $NMe_2$ and $CF_3$, and $R^3$ is selected from H or lower alkyl, X is O or S, and Y is C—H or N, or a pharmaceutically acceptable salt thereof. The compounds can be used as protein disulfide isomerase inhibitors. The compounds can also be used in a method of treating or cancer in a subject.

(I)

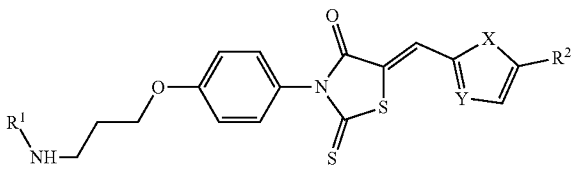

7 Claims, 11 Drawing Sheets

| DRUG NAME | IC50, $\mu$M | CHEMICAL STRUCTURE | ClogP | LogS |
|---|---|---|---|---|
| 642_34 | 0.12 |  | 4.056 | -7.208 |
| 642_35 | 0.15 |  | 4.953 | -7.531 |
| 642_37 | 0.18 |  | 4.066 | -6.461 |
| 642_38 | 0.32 |  | 3.399 | -6.299 |
| 642_39 | 8.31 |  | 1.895 | -5.48 |
| 642_40 | 3.06 |  | 3.3526 | -5.295 |
| 642_41 | 0.39 |  | 3.3526 | -5.795 |
| 642_34-AMINE | N/D |  | 3.196 | -6.802 |

A

B

C

D $R^1$ = Trp, Tyr, Ala, Pro

BIOAVAILABLE PROTEIN DISULFIDE ISOMERASE INHIBITORS

CROSS-REFERENCE TO RELATED APPLICATIONS

This application claims priority from U.S. Provisional Application Ser. No. 63/070,855 filed Aug. 27, 2020, which is incorporated herein by reference.

BACKGROUND

Multiple myeloma (MM) is a genetically complex hematological malignancy which is characterized by clonal proliferation of plasma cells in the bone marrow and secretion of monoclonal antibodies and cytokines that can damage bone, bone marrow, and kidney function. Manier et al., Nat. Rev. Clin. Oncol., 14, 100-113 (2017). Although clinical outcomes continue to improve with introduction and investigation of novel agents, the presence of genetically heterogeneous sub-clones essentially precludes cure. Weiss et al., Blood, 113, 5418-5422 (2009). Per SEER estimates, MM was the cause of death for 12,830 individuals in the US in 2020, while 32,270 were newly diagnosed.

MM cells carry the highest protein synthesis and secretory burden of all mammalian cells, amplifying the high dependence on the unfolded protein response in cancer to a degree where proteasome inhibition provided a major breakthrough. Hideshima et al., Cancer Res., 61, 3071-3076 (2001). Despite the success of proteasome inhibitors and other recently approved drugs, including CD38-targeting antibodies, MM remains incurable in most patients. Importantly, the refractory state to current drugs portends poor median survival below 6 months, indicating a persistent unmet medical need. Gandhi et al., Leukemia, 33, 2266-2275 (2019) The secretion of large quantities of immunoglobulin (Ig) and cytokines by myeloma cells requires rearrangement of intramolecular disulfide bonds after their translation from mRNA. Ribatti, D., Immunol. Lett., 164, 59-68 (2015) Protein disulfide isomerases (PDIs) are the only enzymes to meet this need through their reductase, oxidase, and isomerase functions (Kersteen et al., Antioxid. Redox Signal., 5, 413-424 (2003)), and PDIA1 is the main endoplasmic reticulum (ER) resident isoform of this multifunctional protein family. Laurindo et al., Free. Radic. Biol. Med., 52, 1954-1969 (2012) PDIA1 is upregulated in multiple malignancies such as melanoma, lymphoma, hepatocellular carcinoma, brain, kidney, ovarian, prostate, and lung cancers. Xu et al., Drug Discov. Today, 19, 222-240 (2014) The ER-based functions of PDIA1 as integral parts of the unfolded protein response have been linked to the "Achilles heel" of MM. Vincenz-Donnelly et al., Mol. Cancer Ther., 12, 831-843 (2013) High protein synthesis, nutrient deficiency, and hypoxia in MM cause the ER to function at maximum capacity where perturbation results in cell death. To date, this has only been exploited clinically through proteasome inhibition, suggesting that targeting additional adaptive responses may help counteract the proteasome inhibitor refractory state and provide new myeloma selective treatment options.

Previously, the inventors and their colleagues reported the identification of a PDI inhibitor (CCF642) from a phenotypic multilayered MM cell-based cytotoxicity assay that modeled disease niche, normal liver, kidney, and bone marrow. Vatolin et al., Cancer Res., 76, 3340-3350 (2016). CCF642 covalently modified the catalytic site lysine residue leading to PDIA1 inactivation, inducing irreversible lethal ER stress and hence elimination of MM cells both in vitro and in vivo with no apparent adverse effects on normal bone marrow cells. In addition, CCF642 maintains its therapeutic effect against bortezomib (BTZ)-resistant MM cells through PDIA1 inhibition. However, CCF642 has poor solubility and suboptimal selectivity precluding clinical translation. Accordingly, their remains a need for PDI inhibitors useful for the treatment of multiple myeloma.

SUMMARY OF THE INVENTION

Multiple myeloma is a genetically complex hematologic neoplasia in which malignant plasma cells constantly operate at the maximum limit of their unfolded protein response (UPR) due to a high secretory burden of immunoglobulins and cytokines. The endoplasmic reticulum (ER) resident protein disulfide isomerase, PDIA1 is indispensable for maintaining structural integrity of cysteine-rich antibodies and cytokines that require accurate intramolecular disulfide bond arrangement. PDIA1 expression analysis from RNA-seq of multiple myeloma patients demonstrated an inverse relationship with survival in relapsed or refractory disease, supporting its critical role in myeloma persistence. Using a structure-guided medicinal chemistry approach, the inventors developed a potent, orally bioavailable small molecule PDIA1 inhibitor CCF642-34. The inhibition of PDIA1 overwhelms the UPR in myeloma cells, resulting in their apoptotic cell death at doses that do not affect the normal CD34+ hematopoietic stem and progenitor cells. Bortezomib resistance leads to increased PDIA1 expression and thus CCF642-34 sensitivity, suggesting that proteasome inhibitor resistance leads to PDIA1 dependence for proteostasis and survival. CCF642-34 induces acute unresolvable UPR in myeloma cells, and oral treatment increased survival of mice in the syngeneic 5TGM1 model of myeloma. Results support development of CCF642-34 to selectively target the plasma cell program and overcome the treatment-refractory state in myeloma.

DETAILED DESCRIPTION OF THE INVENTION

Figure 1:
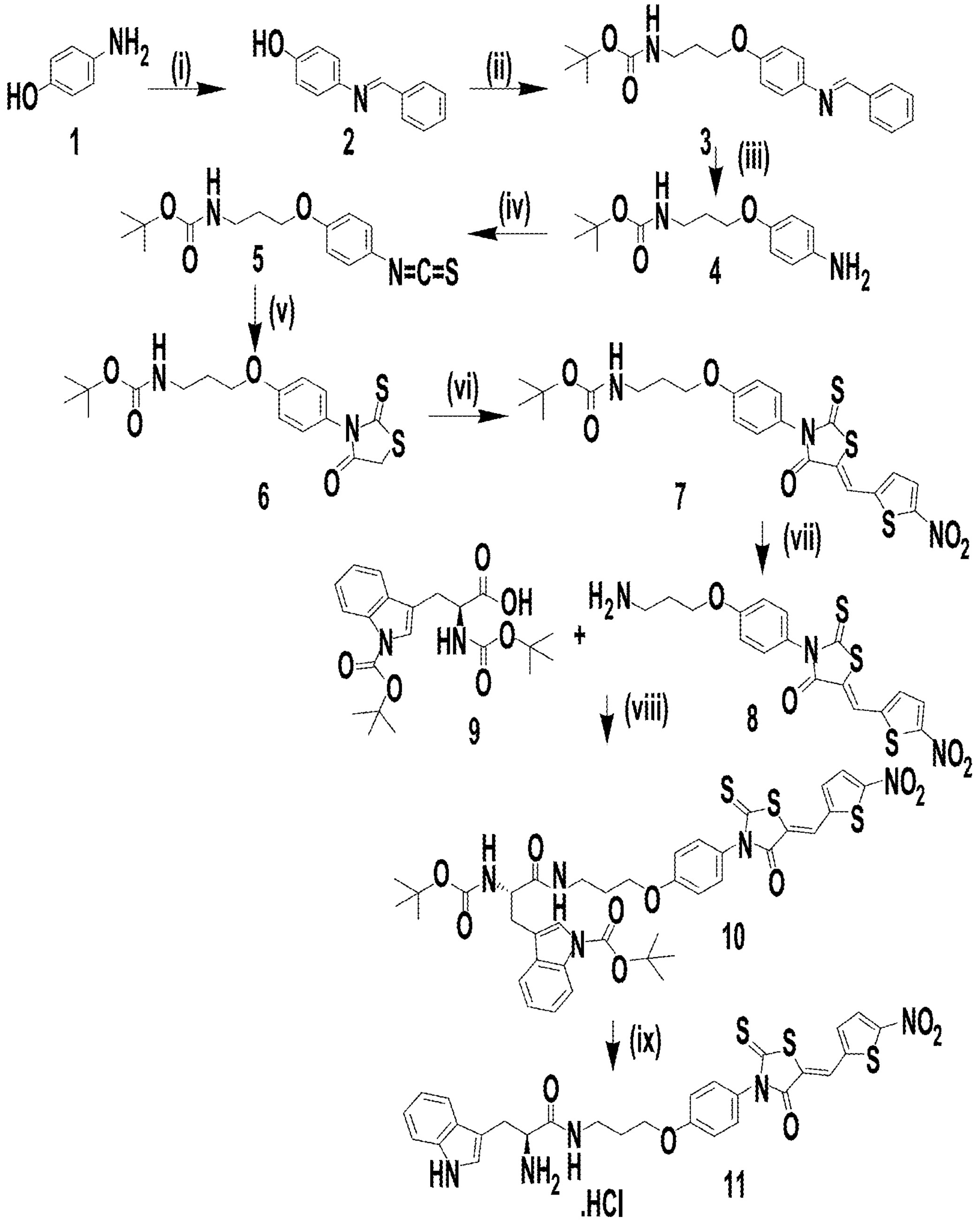
FIG. 1 provides a chemical synthesis scheme of CCF642 analogues.

The present invention provides compounds according to formula I:

(I)

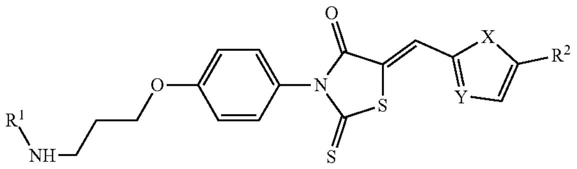

wherein $R^1$ is an amino acid or a modified amino acid linked to the compound through a peptide bond, $R^2$ is selected from CN, $SO_2CH_3$, $NO_2$, $CO_2R^3$, $CONHR^3$, $NH_2$, $NMe_2$ and $CF_3$, and $R^3$ is selected from H or lower alkyl, X is O or S, and Y is C—H or N, or a pharmaceutically acceptable salt thereof. The compounds can be used as protein disulfide isomerase inhibitors. The compounds can also be used in a method of treating or cancer in a subject.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for protein disulfide isomerase inhibitors are those that do not interfere with the compounds anticancer activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A heterocyclyl group means a mono- or bicyclic ring system in which one or more carbon atoms can be replaced by one or more heteroatoms such as, for example, 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula $—C(O)—NR_2$ each R group is independently selected.

The terms "group" and "moiety" are used herein to differentiate between chemical species that allow for substitution or that may be substituted and those that do not so allow for substitution or may not be so substituted. Thus, when the term "group" is used to describe a chemical substituent, the described chemical material includes the unsubstituted group and that group substituted with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment also includes partial or total destruction of the undesirable proliferating cells with minimal destructive effects on normal cells. In accordance with the present invention, desired mechanisms of treatment at the cellular include, but are not limited to one or more of apoptosis, cell cycle arrest, cellular differentiation, or DNA synthesis arrest.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those having an enhanced risk of developing precancers and cancers. An elevated risk represents an above-average risk that a subject will develop cancer, which can be determined, for example, through family history or the detection of genes causing a predisposition to developing cancer.

"Pharmaceutically acceptable" as used herein means that the compound or composition is suitable for administration to a subject to achieve the treatments described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as the inhibition of protein disulfide isomerase by a detectable amount.

The term "subject" for purposes of treatment includes any human or animal subject who has a disorder characterized by unwanted, rapid cell proliferation. Such disorders include, but are not limited to cancers and precancers. For methods of prevention the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. In some embodiments, the subject is a human.

Bioavailable Protein Disulfide Isomerase Inhibitors

In one aspect, the invention provides compounds according to formula I (I)

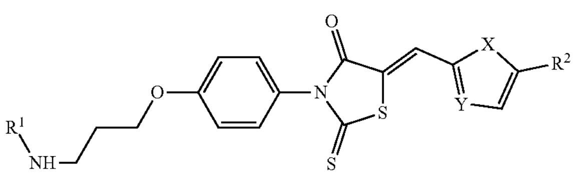

wherein: $R^1$ is an amino acid or a modified amino acid linked to the compound through a peptide bond, $R^2$ is selected from CN, $SO_2CH_3$, $NO_2$, $CO_2R^3$, $CONHR^3$, $NH_2$, $NMe_2$ and $CF_3$, $R^3$ is selected from H or lower alkyl, X is O or S, and Y is C—H or N, or a pharmaceutically acceptable salt thereof.

The compounds of formula I are protein disulfide isomerase inhibitors that include an amino acid or modified amino acid that preferably improves their bioavailability. Protein disulfide isomerases (PDIs) are enzymes that facilitate the rearrangement of intramolecular disulfide bonds after the translation of proteins from mRNA to enable proper protein folding. Protein disulfide isomerase inhibitors bind to the enzyme, and thereby reduce the compatibility of the enzyme with its substrates, preventing or decreasing the catalysis of reactions normally facilitated by the enzyme. Protein disulfide-isomerase has two catalytic thioredoxin-like domains (active sites), each containing the canonical CGHC motif, and two non-catalytic domains. A number of PDIs are known. Protein disulfide isomerase family A includes members 1, 2, 3, 4, 5, and 6. PDIA1 is the main endoplasmic reticulum (ER) resident isoform of this protein family.

The group $R^1$ of the compounds of formula I is an amino acid or a modified amino acid linked to the compound through a peptide bond. More specifically, the carboxyl functional group of the amino acid forms an amide with the secondary amine adjacent to $R^1$. Amino acids are organic compounds that contain amino (—$NH_2$) and carboxyl (—COOH) functional groups, along with a side chain (R group) specific to each amino acid, and have the general formula: $NH_2$—CRH—COOH, where R, the side chain, is H or an organic group. Where R is an organic group, R can be either polar or nonpolar (i.e., hydrophobic). About 500 naturally occurring amino acids are known, though only 20 appear in the genetic code (i.e., the standard amino acids). One method of classifying amino acids is based on the core functional groups' location as alpha- (α-), beta- (β-), gamma- (γ-) or delta- (δ-) amino acids. Preferred amino acids are alpha amino acids, which include the well known 22 proteinogenic amino acids. Proteinogenic amino acids are typically found in the L-stereoisomer form. Proteinogenic amino acids include arginine, histidine, lysine, aspartic acid, glutamic acid, serine, threonine, asparagine, glutamine, cysteine, selenocysteine, pyrrolysine, glycine, proline, alanine, isoleucine, leucine, methionine, phenylalanine, tryptophan, tyrosine, and valine. In some embodiments, $R^1$ is selected from the group consisting of histadine, tyrosine, phenylalanine, and tyrosine. In some embodiments, $R^1$ is tryptophan, phenylalanine, or tyrosine.

In some embodiments $R^1$ is tryptophan. The structure of the compound wherein $R^1$ is tryptophan is shown below:

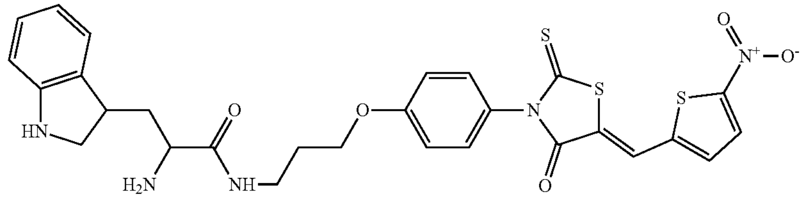

The following abbreviations for amino acids are used throughout the application: A=Ala=Alanine, T=Thr=Threonine, V=Val=Valine, C=Cys=Cysteine, L=Leu=Leucine, Y=Tyr=Tyrosine, I=Ile=Isoleucine, N=Asn=Asparagine, P=Pro=Proline, Q=Gln=Glutamine, F=Phe=Phenylalanine, D=Asp=Aspartic Acid, W=Trp=Tryptophan, E=Glu=Glutamic Acid, M=Met=Methionine, K=Lys=Lysine, G=Gly=Glycine, R=Arg=Arginine, S=Ser=Serine, H=His=Histidine.

Modified amino acids include amino acids which have been chemically modified so that they have minor differences from the natural form. Modified amino acids include those formed by posttranslational modified such as phosphorylated amino acids, and the modified amino acid y-carboxyglutamic acid. Modified amino acids also include those that have been chemically modified to substitute or remove a single atom or functional group from the amino acid, or to change the stereochemistry of the amino acid. For example, in some embodiments, modified amino acids include those in which the primary amino group has been removed. An example of a protein disulfide isomerase inhibitor including a modified amino acid in which the primary amino group has been removed is shown below:

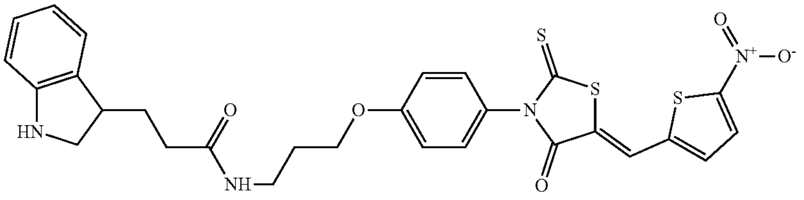 [SMILES: O=C(CCC1CNc2ccccc21)NCCCOc1ccc(N2C(=O)/C(=C/c3ccc([N+](=O)[O-])s3)SC2=S)cc1]

The protein disulfide isomerase inhibitors described herein have been modified to improve their bioavailability. Bioavailability is a subcategory of absorption and is generally defined as the fraction of an administered dose of unchanged drug that reaches the systemic circulation. Improved bioavailability generally results from compounds having improved solubility in aqueous solution. Many drugs such as protein disulfide isomerase inhibitors are hydrophobic and suffer from poor bioavailability when administered (e.g., orally). The bioavailability of the PDI inhibitors described herein is improved relative to the PDI inhibitors previously described by the inventors in U.S. Pat. No. 9,359,342 and Vatolin et al., Cancer Res., 76, 3340-3350 (2016).

The group $R^2$ can be selected from a variety of different functional groups. In some embodiments, $R^2$ is selected from CN, $SO_2CH_3$, $NO_2$, $CO_2R^3$, CONHR, $NH_2$, $NMe_2$ and $CF_3$. When $R^2$ is $CO_2R^3$ or $CONHR^3$, $R^3$ is selected from H or lower alkyl. In some embodiments, $R^2$ is $NO_2$.

The compound of formula I also includes two variable positions (X and Y) in the heteroaryl group adjacent to $R^2$. The variable position X can be O or S, and the variable position Y can be C—H or N. In some embodiments, X is S and Y is C—H.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

Another aspect of the invention provides a method of treating or cancer in a subject in need thereof by administering to the subject a therapeutically effective amount of a compound of Formula I:

(I)

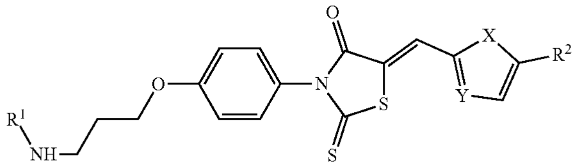

wherein: $R^1$ is an amino acid or a modified amino acid inked to the compound through a peptide bond, $R^2$ is selected from CN, $SO_2CH_3$, $NO_2$, $CO_2R^3$, $CONHR^3$, $NH_2$, $NMe_2$ and $CF_3$, and $R^3$ is selected from H or lower alkyl, X is O or S, and Y is C—H or N, or a pharmaceutically acceptable salt thereof. The compounds used in the method can include any of the protein disulfide isomerase inhibitors described herein.

In some embodiments, $R^1$ is tryptophan, phenylalanine, or tyrosine, while in further embodiments $R^1$ is tryptophan. In some embodiments, $R^2$ is $NO_2$, while in further embodiments X is S and Y is C—H. In some embodiments, the compound is administered orally, and in some embodiments the subject is human.

In some embodiments, the compound has the structure:

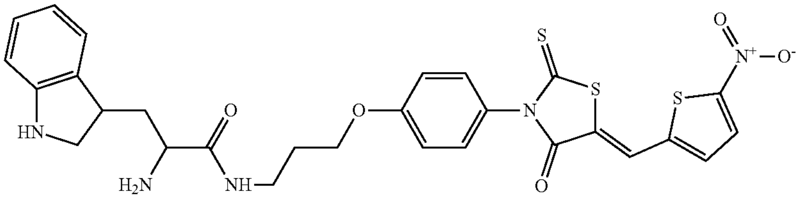

Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of leukemia, non-small cell lung cancer, colon cancer, central nervous system cancer, melanoma, ovarian cancer, renal cancer, prostate cancer, and breast cancer. In some embodiments, the cancer is myeloma or lymphoma.

Cancer can be treated or prevented by regulating signaling pathways within the cancerous or potentially cancerous cells to prevent excessive growth or provide regulation of other aberrant processes within the cells. While not intending to be bound by theory, the compounds of the present invention can treat or prevent cancer by causing protein ubiquitination and degradation by inhibiting the main enzyme responsible for post-translational folding in the endoplasmic reticulum; protein disulfide isomerase. Protein disulfide isomerase is known to play a role in a wide variety of different types of cancer, and therefore its inhibition can be expected to treat a wide variety of different types of cancer. Xu et al, Drug Discovery Today, 19(3):222-240 (2014). Accordingly, one aspect of the present invention provides a method of increasing ubiquitination in a cell by contacting the cell with a compound of formula I or a pharmaceutically acceptable salt thereof. The cell can be contacted in vivo, in vitro, or ex vivo. In some embodiments, the contacted cell can be a cancer cell.

Accumulation of misfolded proteins characterizes a number of diseases other than cancer. For example, misfolded protein accumulation occurs in neurodegenerative diseases such as Alzheimer's disease, and also occurs in cardiac disorders. Accordingly, some embodiments of the invention are directed to the use of protein disulfide isomerase inhibitors to treat diseases involving excessive accumulation of misfolded proteins.

The bioavailable protein disulfide isomerase inhibitors described herein can be administered prophylactically to a mammal prior to the development of cancer. Prophylactic administration, also referred to as prevention, is effective to decrease the likelihood that cancer will develop in the subject. Alternatively, the bioavailable protein disulfide isomerase inhibitors can be administered therapeutically to a subject that already has cancer. In one embodiment of therapeutic administration, administration of the bioavailable protein disulfide isomerase inhibitors is effective to eliminate the cancer; in another embodiment, administration of the bioavailable protein disulfide isomerase inhibitors is effective to decrease the symptoms or spread of the cancer.

The effectiveness of cancer treatment may be measured by evaluating a reduction in tumor load or decrease in tumor growth in a subject in response to the administration of the ubiquitin-activating agent. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Methods of cancer treatment using the compounds described herein can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

Chemotherapy can include administering an additional anticancer agent to the subject. Examples of anticancer agents that can be co-administered with the compounds of the present invention for cancer treatment include alkylating agents, antimetabolites, natural products, hormones and antagonists, and miscellaneous agents. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-niercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include *vinca* alkaloids such as vinblastine (VLB) and vincristine; taxanes such as paclitaxel (Abraxane) and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interleukin 2. Examples of hormones and antagonists include luteinizing releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (czs-DDP), oxaliplatin and carboplatin; anthracenediones such as mitoxantrone; substituted ureas such as hydroxyurea; methylhydrazine derivatives such as procarbazine (N-methylhydrazine, MIH); proteosome inhibitors such as bortezomib, and aminoglutethimide; RXR agonists such as bexarotene; and tyrosine kinase inhibitors such as imatinib.

Administration and Formulation

In some embodiments, the compound of formula I is provided together with a pharmaceutically acceptable carrier to provide a pharmaceutical composition. Pharmaceutical compositions include protein disulfide isomerase inhibitors according to formula I as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The protein disulfide isomerase inhibitors can be administered as pharmaceutically acceptable salts. Pharmaceutically acceptable salt refers to the relatively non-toxic, inorganic and organic acid addition salts of the protein disulfide isomerase inhibitors. These salts can be prepared in situ during the final isolation and purification of the protein disulfide isomerase inhibitor, or by separately reacting a purified protein disulfide isomerase inhibitor with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions includes one or more protein disulfide isomerase inhibitors together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, albumin, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The protein disulfide isomerase inhibitors can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the active agent, or as a solution or suspension in an aqueous liquor or non-aqueous liquid such as a syrup, an elixir, an emulsion, or a draught. Such compositions and preparations typically contain at least about 0.1 wt-% of the active agent. The amount of protein disulfide isomerase inhibitor (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wisconsin, USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie,* 4, Aufl. Ed. Springer-Verlag, Berlin, Germany, including supplements (also available via the Beilstein online database)).

A specific reaction scheme for preparing the compounds of the present invention is provided by FIG. 1, with further supporting description included in the Example. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following example. It is to be understood that the particular example, materials, amounts, and procedures are to be interpreted broadly in accordance with the scope and spirit of the invention as set forth herein.

EXAMPLE

Example 1: Therapeutic Targeting of Protein Disulfide Isomerase PDIA1 in Multiple Myeloma This example shows that expression of PDIA1 inversely correlates with survival in relapsed and refractory myeloma patients. Using structure-guided medicinal chemistry, the inventors developed a new analogue of CCF642. The new PDIA1 inhibitor, CCF642-34, specifically binds and inhibits PDIA1. Unlike CCF642, it has improved drug-like properties, including improved solubility, selectivity, and potency, and is effective when administered orally in an aggressive syngeneic mouse model of myeloma.

Materials and Methods

Cells and reagents: MM1.S-luc-BTZ (BTZ®)-resistant cell line was made in our laboratory. Starting with 1 nM concentration, MM1.S-luc cells were treated with BTZ and exposed continuously for 5 days and removed for 2 days before re-exposure to the drug until the growth of the cells mimicked the parental cell line. Incremental increase of the drug was applied until the concentration of 8 nM was reached. Cell lines were grown according to the guidelines by the supplier and used within 10 passages in fresh culture. di-E-GSSG was from IMCO Corp. Ltd. IMDM and RPMI-1640 cell culture media were from Cleveland Clinic media core services. BTZ was procured from Millennium Pharmaceuticals Inc. All cell lines that are used in this study and their detailed information are shown in table 1 below.

TABLE 1

Cell line and Culture Conditions

| Cell Line | Organism | Disease | Source | Media |
|---|---|---|---|---|
| MM1.S.luc | human | IgA lambda myeloma | ATCC | RPMI-1640 * |
| MM1.S.luc $Btz^R$ | human | Ig A lambda myeloma | CCF Lab | |
| RPMI-8226 | human | Plasmacytoma; myeloma | ATCC | |
| 5TGM1-luc | murine | Plasmacytoma; myeloma | Gift from Dr. Oyajobi [13] | IMDM * |

* All cell culture media contained 10% fetal bovine serum (FBS, Bio-Techne Cat #S11150) and 1% P/S.

Cell viability assay: Cell viability was measured in 96 well culture plates ($2\times10^4$ cells/well) using CellTiter-Glo® Luminescent Cell Viability Assay (Promega, Madison, WI, USA) according to the manufacturer's protocol.

In vitro colony-forming assays: Mononuclear cells derived from bone marrow or purified CD34+ cells from a healthy donor, cord blood, or MM cell RPMI-8226 were grown in semi-solid methylcellulose media (MethoCult™, H4435; STEMCELL Technologies) in the presence of indicated compounds and concentrations. A total of 10,000/mL normal bone marrow CD34+ cells and 1000/mL RPMI-8226 cells were plat-ed, and colonies were scored on day 14.

Immunoblotting: Immunoblotting was performed as described previously (Dallas et al., Blood, 93, 1697-1706 (1999)) using primary antibodies against PDIA1 (Cat #3501), XBP1-S (Cat #12782); IRE1α (Cat #3294), C/EBP homologous protein (CHOP) (Cat #5554), Caspase-3 (Cat #9665), PARP1 (Cat #9542), and GAPDH (Cat #3683) purchased from Cell Signaling Technology, Inc. (Danvers, MA, USA) and used at 1:1000 dilution, unless mentioned otherwise.

Mass spectrometry: Tryptic peptide mixtures were analyzed by online LC-coupled tandem mass spectrometry (LCMS/MS) on an Orbitrap mass spectrometer (Thermo Fisher) as described previously. Gu et al., J. Clin. Investig., 128, 4260-4279 (2018) The Sequest software was used to perform database searches, using the Extract_msn.exe macro provided with Xcalibur (version 2.0 SR2; Thermo Fisher Scientific) to generate peak lists. The following parameters were set for creation of the peak lists: parent ions in the mass range 400-4500, no grouping of MS/MS scans, and threshold at 1000. A peak list was created for each analyzed fraction (i.e., gel slice) and individual Sequest searches were performed for each fraction. The data were searched against *Homo sapiens* entries in the Uniprot protein database. Carbamidomethylation of cysteines was set as a fixed modification, and oxidation of methionine was set as a variable modification. Specificity of trypsin digestion was set for cleavage after lysine or arginine, and two missed trypsin cleavage sites were al-lowed. The mass tolerances in MS and MS/MS were set to 10 ppm and 0.6 Da, respectively, and the instrument setting was specified as "ESI-Trap."

Medicinal chemistry: All of the new PDI inhibitors reported in FIG. 2 and represented by the generic structure in results were prepared in similar fashion following the chemistry scheme shown for 642-34 in FIG. 1 and described in detail earlier. Vatolin, et al., Cancer Res., 76, 3340-3350 (2016) The 7 step preparation of the HCl salt of primary amine intermediate 8, which follows standard literature described procedures, begins with synthesis of the benzaldehyde-derived Schiff base 2 of commercially available 4-amino phenol 1 via reflux in excess trimethyl orthoformate. Alkylation of the phenol of 2 with 3-(BOC-amino) propyl bromide in dry DMF and 3 equivalents of cesium carbonate at 50° C. for 15 h gave 3. Catalytic reduction and hydrogenolysis with $Pd(OH)_2$ and ammonium formate in refluxing ethanol provided aromatic amine 4. Treatment of 4 with thiophosgene in 1:1 dichloromethane/water gave the crude isothiocyanate 5, which upon reaction with methyl thioglycolate in dichloromethane in the presence of triethylamine afforded the thiazolidinone 6. Condensation of the thiazolidinone 6 with 5-nitro-thiophene-2-carboxaldehyde in acetic acid in the presence of 5 equivalents of sodium acetate at 90° C. for 16 h provided the substituted N-BOC-protected rhodanine 7 upon cooling and precipitation with the addition of water. N-BOC deprotection with excess 4N HCl in dioxane at room temperature (20° C.) for 2 h provided the key inter-mediate HCl salt 8, which was used to make the 7 analogues shown in Supplemental Table S1. The coupling of 8 with the requisite L-amino acids was accomplished in dry DMF with Hexafluorophosphate Azabenzotriazole Tetramethyl Uronium, (HATU, 1-[Bis(dimethylamino)methylene]-1H-1,2,3-triazolo[4,5-b]pyridinium 3-oxid hexafluorophosphate) and 2 equivalents of Hunig's base and gave the penultimate intermediates. The final compounds CCF642-34 through CCF642-41 were prepared by treatment with excess 4N HCl in dioxane at room temperature. The biotin derivative CCF642-34-biotin was synthesized from the HCl salt of CCF642-34 by treatment with biotin in DMF with HATU and Hunig's base. All final compounds showed $^{1}H$, $^{13}C$ NMR, and Mass Spec analyses consistent with assigned structure.

Computational modeling and molecular dynamics: The computational model used the reduced PDI (NP_000909.2) crystal structure (Wang et al., Antioxid. Redox Signal., 19, 36-45 (2013)) for binding of CCF642 and biotinylated CCF642-34 to PDIA1. Initial docking of CCF642 and its analogues on PDI (PDB ID: 4EKZ) was performed by using AutoDock 4.1 (in AutoDock Tools 1.5.2) as described previously. Vatolin et al., Ibid. Binding energy calculations used CHARMM force field in Discovery Studio 1.3 pipeline (Accelrys, Inc.). The predicted structure of PDIA1-CCF642 covalent complex was used for the generation of structure-activity relationships that were further probed with in vitro enzyme activity assays.

PDI activity: All PDI activity assays were performed using two different substrates, insulin and di-eosin-diglutathione (di-E-GSSG) as described earlier (Vatolin et al., Ibid) with brief modifications. PDIA1 (1 μM) was incubated for 1 h with varying concentrations of PDIA1 inhibitors 642 or 642-34 (0.1, 03, 1, 5, 10, or 20 μM) in 100 mM sodium phosphate pH 7.0, 2 mM EDTA, and 1% DMSO. Bovine insulin (100 μM) and DTT (1 mM) were added to initiate the reaction. Kinetic readings were taken every minute for 2 h at 650 nm absorbance using a BioTek Synergy plate reader (BioTek Instruments, Inc., Winooski, VT, USA). For highly sensitive fluorescence-based assays, di-E-GSSG as a pseudo substrate was utilized to access the activity of PDIA1. Raturi, A.; Mutus, B., Free. Radic. Biol. Med., 43, 62-70 (2007) Known concentrations of recombinant PDIA1 were mixed with 10 mM GSH and incubated at 37° C. for 30 min in 150 mM $K_2HPO_4/KH_2PO_4$ (pH 7.1) buffer solution. PDI inhibitor was added into the mixture and incubated for an additional 30 min at 37° C. Di-E-GSSG was added into the reaction mix at a final concentration of 100 nM and samples were transferred into white multi-well plates (Becton Dickson Labware, Franklin Lakes, USA). Synergy H1 plate reader (BioTek, WI, USA) was used for kinetic analysis using excitation at 518 nm, emission at 545 nm, reads of 0.1 sec/well every minute at 25° C. for 1 h. Baseline fluorescence was determined from di-E-GSSG reactions without PDI and GSH.

Enzyme kinetics and data analysis: All kinetic analysis was performed using irreversible inhibition methods described earlier. Singh et al., Nat. Rev. Drug Discov., 10, 307-317 (2011). Ki, the inactivation constant, and k2, the rate of inactivation, were calculated according to PDI activity at different drug concentrations defined as total occupancy of the active site at exp($k_{obs}$*time) and the $k_{obs}$=k2 [I]/(Ki+[I]) for the reaction assuming the following equation:

$$E+I \underset{Ki}{\rightleftharpoons} [E*I] \xrightarrow{k_2} E\,I;$$

where E is the enzyme, I is the PDIA1 inhibitor, Ki is the inactivation constant, and k2 the rate of inactivation. All curve fitting and analyses were performed in GraphPad Prism.

PDIA1 purification: Recombinant human PDIA1 (Acc #P07237) was cloned into expression vector pET6×HN-N (Clontech Laboratories, Inc., Ann Arbor, MI) by using Sal1 and Not1 restriction enzymes after amplification with primers that contained Sal1 and Not1 digestion sites. The pET6×HN-PDIA1 was expressed using the *Escherichia coli* strain BL21 (DE3) NiCo (NEB cat #C2529H). This plasmid encodes a fusion protein containing the entire human PDI sequence with an N-terminal His6 tag. Recombinant PDI was purified from the soluble fraction of the cell lysate using His60 Ni Superflow resin (Clontech Laboratories, Inc.). Bound PDI was eluted according to the user's manual (Clontech Laboratories, Inc.) Protein quantification was performed by the Bradford assay.

Liver microsome assay: 20 μM CCF642 or CCF642-34 were incubated with 1 mM NADPH and 0.25 mg/mL human liver microsomes (Sigma, Cat. No: M0567) at 37° C. Human liver microsomes were precipitated by quenching the reaction into ice-cold acetonitrile at indicated time points. Supernatant was obtained after centrifugation at 15,000 g for 5 min and the remaining compound in supernatant was analyzed by Agilent 1260 Infinity II HPLC with Ultra-violet (UV) detector using Gemini column, 3 μM particle size 150×2 mm (Phenomenex). A gradient of 50/50 acetonitrile/water with 0.1% (v/v) formic acid was run isocratically for 2 min at 0.3 mL/min flow while maintaining 55° C. column temperature. A gradient of the 90/10 acetonitrile/water with 0.1% (v/v) formic acid at 0.3 mL/min flow was introduced from 3 min to 13 min. A gradient of 50/50 acetonitrile/water with 0.1% (v/v) formic acid then ran isocratically for 2 min with the same flow rate, followed by a gradient increase to 100% acetonitrile over 2 min to store the column. The relative amount of drug at each time point was determined by using the UV peak detection at wavelength 254 and 282 nm. This was compared with the control run where human liver microsomes were not present in order to determine remaining drug percentage. Each HPLC-UV run was performed in duplicate.

ROS detection: MM1.S, MM1.S.LUC, and BTZ-resistant MM1.S.LUC cells were washed with DPBS and treated with 5 μM carboxy-H2DCFDA (Molecular Probes) for 45 min at 37° C. The cells were then washed 3 times in DPBS and followed by 2.5 μM CCF642-34 treatment up to 4 h. After the incubation, the cells were washed 3 times and the intracellular ROS was quantified (excitation=493 nm; excitation=523 nm) using a BioTek Synergy plate reader (BioTek Instruments, Inc., Winooski, VT, USA).

RNA-seq and analysis: MM1.S cells were treated with 3 μM of either CCF642 or CCF642-34 for 6 h, and RNA was purified by using the NucleoSpin RNA kit (Takara Bio USA, Inc.; cat. #740955) according to the manufacturer's instruction. The RNA sequencings were completed as reported previously. Guan et al., Commun. Biol., 3, 1-13 (2020) The RNA-seq data were sub-mitted to the Gene Expression Omnibus (GEO) repository at the National Center for Biotechnology Information (NCBI) archives, with assigned GEO accession number GSE167097.

Mouse experiment: Animal care and procedures were conducted in accordance with institutional guidelines approved by the Institutional Animal Care and Use Committee (IACUC). The C57BL/KaLwRij mice (Harlan laboratories) were injected with 5TGM1-luc cells via tail vein. After the first day of engraftment, the mice were randomized and either treated with CCF642-34 per oral gavage (20 mg/kg) or with control vehicle (10% 2-hydroxy-propyl-β-cyclodextrin) three times a week for 8 weeks.

Myeloma patient database: In patients with plasma cell disorders who consented to Total Cancer Care® Moffitt Cancer Center research sample protocol #14690, IRB #Pro 00014441, CD138 magnetic bead purified bone marrow cells obtained during routine clinical bone marrow exams were submitted to RNA sequencing and results were annotated with key clinical variables such as plasma cell disorder type, number of prior therapies, survival, and refractory state to individual prior therapies via M2Gen/ORIEN. For the purpose of this manuscript all 689 MM patients from this registry were analyzed for PDIA1 expression and tertiles were subjected to Kaplan-Meier estimates for survival.

Results

Figure 3A:
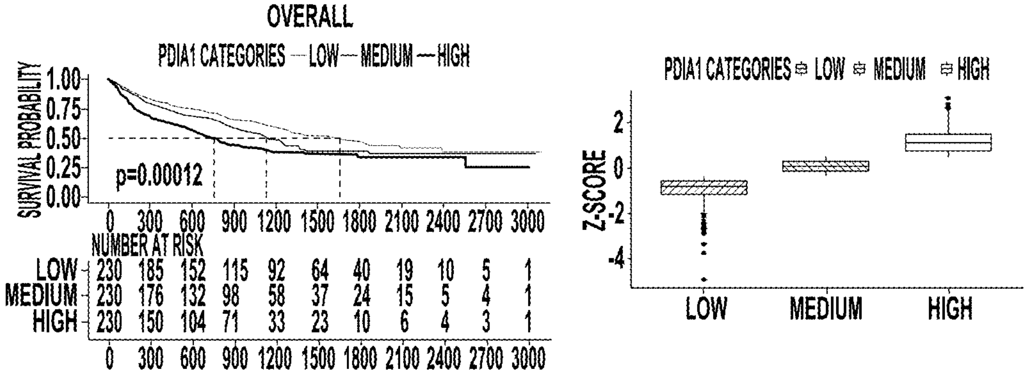
FIGS. 3A-3D provide graphs showing the expression of PDIA1 in myeloma associates with survival. CD138-purified myeloma cells from patients with multiple myeloma were subjected to RNA sequencing and survival was estimated based on Kaplan-Meier for low, medium, and high PDIA1 expression tertiles. The statistical significance for the survival curves was determined by Log-rank test. (A) High and medium expression resulted in inferior survival in the entire myeloma cohort. While (B) no significant effect on survival was seen in newly diagnosed myeloma, in (C) patients with early (1-3 prior lines of therapy) or (D) late relapse (>3 prior lines of therapy) medium and high PDIA1 expression tertile were associated with shorter survival. Abbreviations: NDMM—newly diagnosed multiple myeloma; ERMM—early relapse multiple myeloma; LRMM—late relapse multiple myeloma; os—overall survival.
Figure 3B:
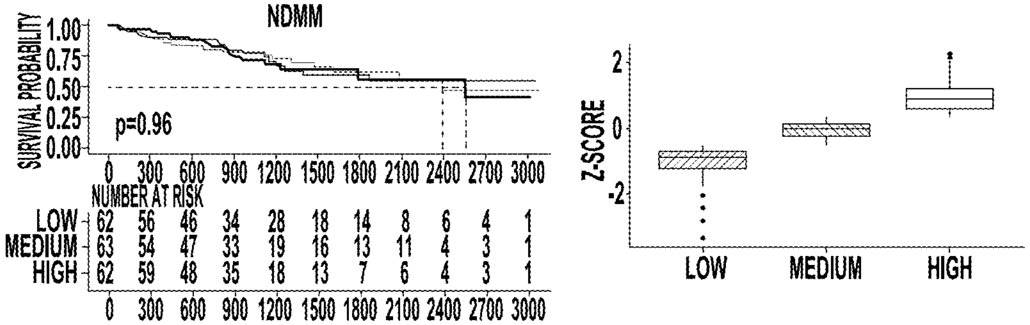
Figure 3C:
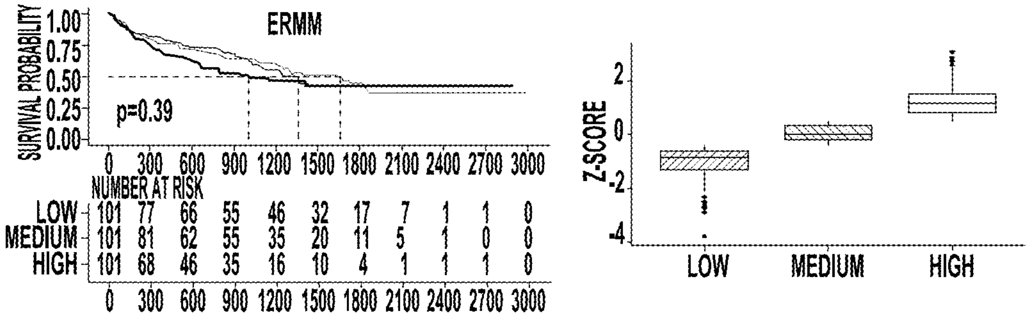
Figure 3D:
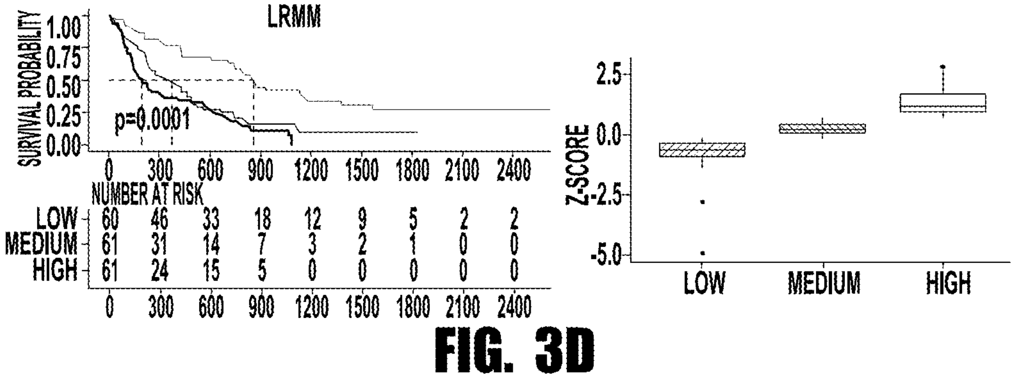

Expression of PDIA1 Inversely Correlates with Survival in Patients with Relapsed or Refractory Myeloma To understand if the PDIA1 expression correlates with survival we analyzed RNA-seq data of CD138-enriched bone marrow cells from MM patients. Among 690 MM patients seen at Moffitt Cancer Center and Research Institute, expression of PDIA1 as assessed by RNA sequencing separated patients into tertiles with significantly (p=0.00012) inferior survival in the two higher tertiles (FIG. 3A). When patients parsed by clinical groups as newly diagnosed myeloma (NDMM), early relapse (ERMM, 1-3 prior lines of therapy), or late relapse (LRMM>3 prior lines of therapy) were analyzed separately, high PDIA1 expression conferred inferior survival in ERMM and LRMM but not NDMM (FIG. 3B-D). This observation suggests that PDIA1 expression may confer adaptive resistance to available treatments. Accordingly, targeting PDIA1 may prove valuable not only because it blocks a very proximal step in the UPR, but, in addition, it may exploit a vulnerability of the resistance phenotype.

Development of a Potent PDIA1 Specific Inhibitor

Figure 2:
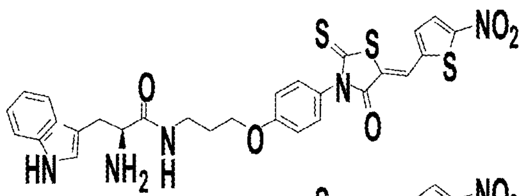
FIG. 2 provides a table showing the physio-chemical properties of CCF642 and its analogues. The physio-chemical properties of CCF642 and its analogues along with IC50 against MM1.S cells are presented. Data is representative of three independent experiments. The IC50 was calculated in GraphPad Prism using nonlinear regression, dose-response inhibition.
Figure 2:
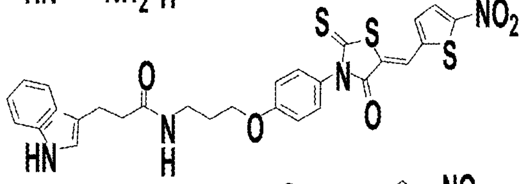
Figure 2:
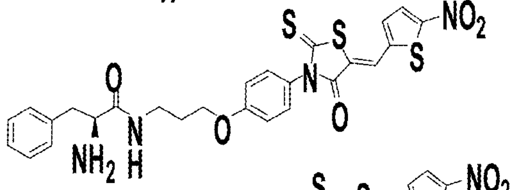
Figure 2:
Figure 2:
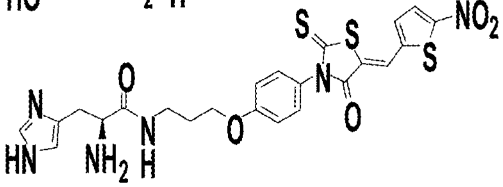
Figure 2:
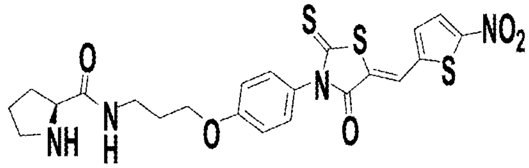
Figure 2:
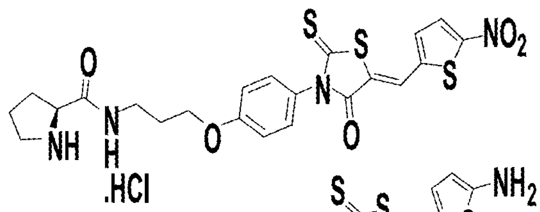
Figure 2:
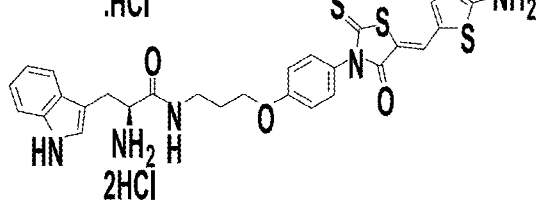
Figure 4A:
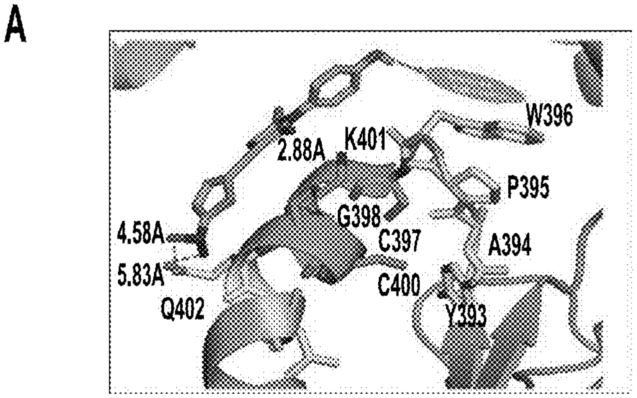
FIGS. 4A-4G provide graphs and images showing that model-based design improves potency and selectivity of protein disulfide isomerase A1 (PDIA1) inhibitors. (A) Ribbon diagram of CCF642-34 docked onto PDIA1. (B) Two-dimensional structure of modified CCF642 pharmacophore, where R represents amino acids tryptophan, tyrosine, phenylalanine, histidine, proline, or alanine. (C) PDIA1/PH4B activity assay was performed in the absence or presence of CCF642 or (D) CCF642-34. In time-dependent inhibition of di-E-GSSG, reduction was monitored for 1 h by the increase in fluorescence, and the relative fluorescence unit was plotted as a function of time. (E-F) The observed rate constant for inhibition, kobs, at each concentration determined from the slope of kinetic data presented in panel C and D. The kobs values are re-plotted against inhibitor concentration and fitted to a hyperbolic equation, kobs=k2[I]/(Ki+[I]), to obtain values for Ki and k2 in GraphPad Prism v8.0.2. The concentration of drug is indicated on each curve, for (E) 642 and (F) CCF642-34. (G) Target validation. Multiple myeloma cells (MM1.S) were treated with vehicle (DMSO) or B-CCF642-34 for 3 h and lysates were separated on SDS-PAGE gel followed by visualization by either anti-PDIA1 antibody or HRP-conjugated streptavidin. The bands' identities are as labeled.
Figure 4B:
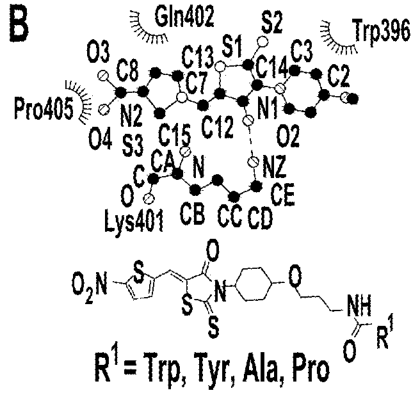
Figure 4C:
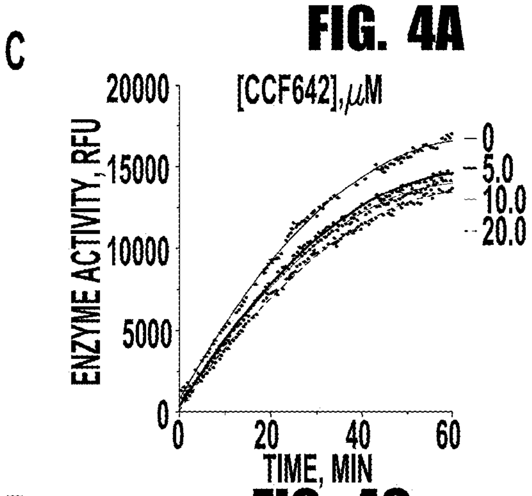
Figure 4D:
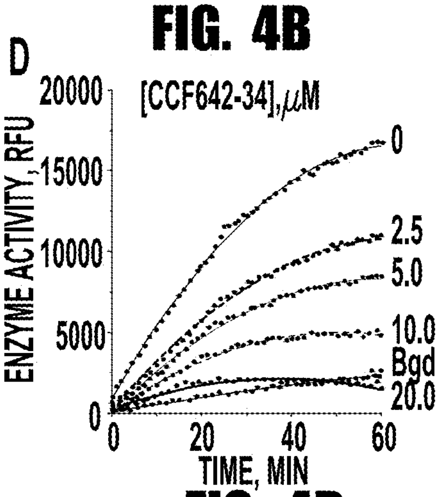
Figure 4E:
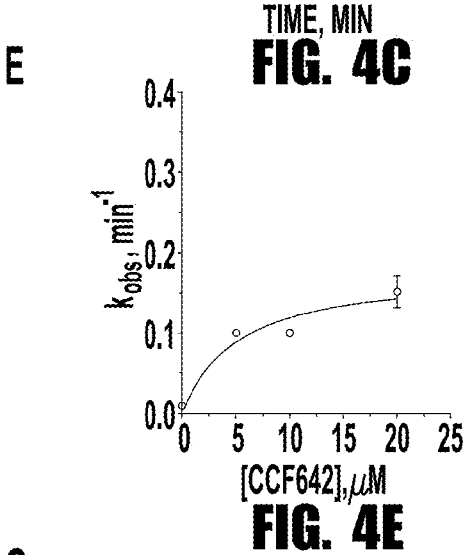
Figure 4F:
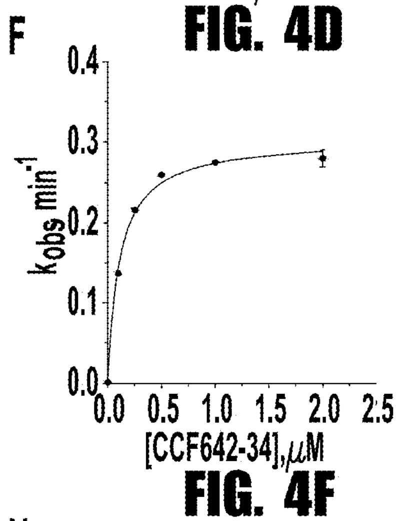

The PDI inhibitor CCF642 was highly potent; however, it was limited for clinical development due to its insolubility and lack of bioavailability. To improve its solubility, potency, and selectivity, the inventors used the CCF642 binding space in the catalytic site for in silico modeling and mapped the binding site to the helix-turn-helix motif composed of the WCGHCK binding site in the aa' and bb' domains of the PDIA1 active site (FIG. 4A,B). The ligand plot analysis of the docked structure of CCF642 with PDIA1 suggested that specific pi stacking interaction with tryptophan W396 could be engaged in the catalytic site with appropriate modifications of the p-methoxy group of the phenyl ring. The inventors chose to accomplish this by attaching a 3-carbon flexible linker with a terminal primary amino group to the corresponding phenol followed by coupling to desired L-amino acids (FIGS. 1, 2, 4A). The N-BOC penultimate intermediates were purified using flash silica gel chromatography and then deprotected using 4N HCl in dioxane to generate the corresponding hydrochloride (HCL) salts. The compounds for testing were fully characterized by $^{1}H$, $^{13}C$ NMR and high-resolution mass spectroscopy. Several of these new amino acid derivatives had increased solubility in aqueous buffer (confirmed in a turbidity assay as well as improved enzyme selectivity in comparison to parent compound CCF642. These results were consistent with their C log P and Log S values (FIG. 2) calculated by Rekker's fragment system approach in ChemDraw. The three different analogues containing tryptophan (CCF642-34), phenylalanine (CCF642-37), or tyrosine (CCF642-38) showed the most specific and up to 10-fold enhanced inhibition of PDIA1 as calculated using two independent substrates in cell free assays. The inactivation constant, $K_{inact}$ of CCF642-34 for PDIA1 was found to be 88±2.8 nM and 100±8.5 nM in di-EGGS and insulin reduction assays, respectively (FIG. 4C-F). The tryptophan analogue CCF642-34 was the most potent PDIA1 inhibitor in different assays among all derivatives of CCF642. Several of the amino acid substitutions, most notably histidine and alanine, were less effective as reflected in the ratio of k2/Ki (FIG. 2), a marker for potency and selectivity. Because CCF642-34 was the most potent analogue in cell free PDI assays (FIGS. 4E, F) and, accordingly, also the most potent in restricting the growth of MM1.S cells (FIG. 2), CCF642-34 was selected as a lead compound for further analysis.

Figure 4G:
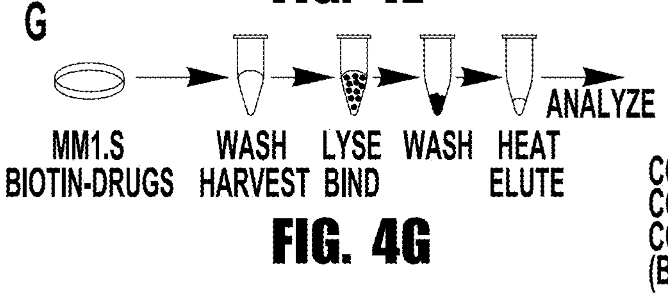
Figure 4H:
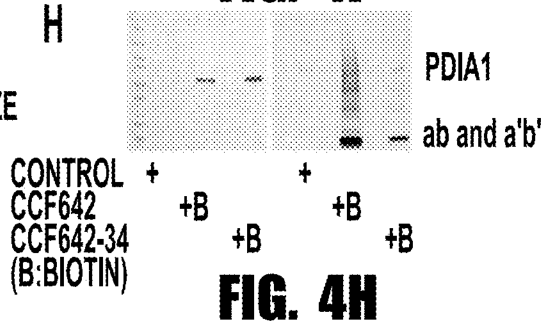

To identify binding partners of CCF642 and CCF642-34, which covalently bind to lysine in the PDIA1 active site, the inventors synthesized biotinylated analogues, CCF642-Biotin and CCF642-34-biotin (FIG. 4G). MM1.S cells were treated with the biotinylated derivatives and the cell lysate probed with streptavidin. As reported previously (Vatolin et al., Ibid), CCF642 has off-target bindings in addition to its binding to PDIA1, however, its analogue CCF642-34 showed remarkable selectivity for PDIA1 (FIG. 4G). When cells were treated for 6 h with CCF642-34-biotin followed by Western blot analysis using either PDIA1 or streptavidin-HRP antibodies, it was demonstrated that PDIA1 was the only specific target that appeared in our analysis (FIG. 4G).

CCF642-34-biotin showed two prominent bands when probed with streptavidin (FIG. 4G). To confirm the identity of these two protein bands, first they were probed with anti-PDIA1 antibodies that showed the only one specific PDIA1 band corresponding to molecular weight 57 kDA, the lower band was not reactive with the PDIA1 antibody used in this assay. To test the identity of the lower band, a streptavidin pull down was performed followed by mass spectral analysis of all proteins. The lower and the upper bands were both PDIA1, as confirmed by the identity of the peptides in LCMS. The inventors were able to map 80.11% and 84.80% peptides of the PDIA1 protein, upper and lower bands, respectively (FIG. 4G). The PDIA1 has two active sites with identical structural arrangements around CGHCK motif, and the lower band's mass spectral analysis confirmed its identity as the full-length protein, therefore, it was concluded that it consisted of the breakdown products of ab and a'b' fragments of PDIA1 that were not recognized by the antibody used in Western blot assays (FIG. 4G). No other protein with significant scoring in LCMS/MS was enriched in a streptavidin pull down of MM1.S cells treated with CCF642-34-biotin, while several other proteins were pulled down with CCF642 as reported previously. Vatolin et al., Ibid.

Figure 5A:
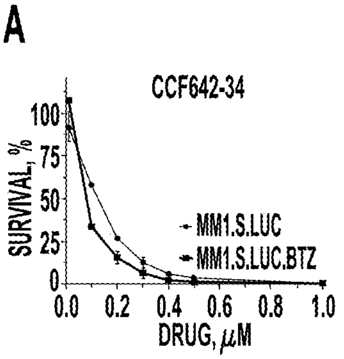
FIGS. 5A-5H provide graphs showing the selective cytotoxicity of PDIA1 inhibitor against multiple myeloma MM1.S cells. Cell vi-ability and LD50 for inhibitors were measured in 96 well culture plates ($2\times10^4$ cells/well) after 72 h of treatment using CellTiter-Glo® Luminescent Cell Viability Assay (Promega, Madison, WI, USA). (A) Cell survival assay with MM1.S.luc and BTZ-resistant MM1.S.luc cells. (B) Bortezomib was used at a fixed IC50 concentration of 2 nM for MM1.S.luc, 8 nM for MM1S.luc BTZ for combined drug toxicity analysis. (C) Comparison of PDIA1 protein levels in MM1.S.luc and MM1.S.luc BTZ-resistant cells. Band intensity was calculated with Image Lab Version 5.2.1. (D) Cell survival assay with 5TGM1.luc and (E) BTZ-resistant 5TGM1.luc cells. (F) MM1.S cell line was exposed to CCF642-34, and BTZ for 72 h for synergistic drug combination test according to Chou and Talalay method. If the fraction of cells affected remained less than 1, the two drugs were determined as synergistic. (G,H) Toxicity of CCF642 and its analogues, CCF642-34 and CCF642-37, against RPMI 8226 and CD34+ normal bone marrow cells from healthy individuals in a colony-forming assay. The number of colony-forming units were plotted for each treatment. The toxicity against normal bone marrow was estimated at ~20-fold over the drugs against multiple myeloma cells.
Figure 5B:
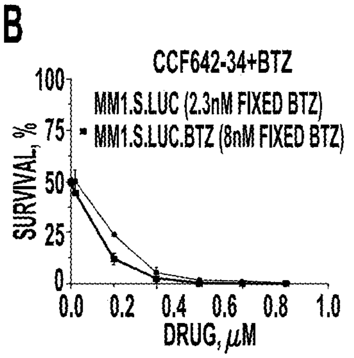
Figure 5C:
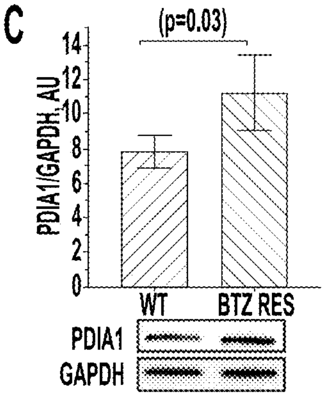
Figure 5D:
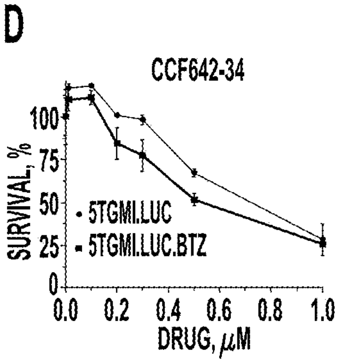
Figure 5E:
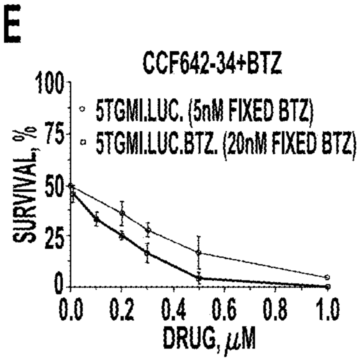

CCF642-34 Inhibits the Growth of Myeloma Cells without Any Significant Effects on Normal Bone Marrow-Derived CD34+ Cells To support the inventors' findings that CCF642 analogues' superior pharmacologic property and PDIA1 selectivity retains their ability to restrict the growth of the MM cells without inducing any adverse effect on normal bone marrow, they determined the LD50 of CCF642-34 against MM cells and found that, during in vitro cell culture, CCF642-34 demonstrated nearly 2-fold higher potency compared to CCF642. The LD50 of CCF642-34 on MM1.S was 118±21 nM compared to 217±19 nM for CCF642 (FIG. 5A). The PDIA1 inhibitor CCF642-34 was also tested on additional multiple myeloma cell lines with different levels of PDIA1; KMS-12-PE, RPMI 8226, and U266, and the LD50 was 165±8, 292±11, and 371±26 nanomolar, respectively.

Consistent with previous reports (Robinson et al., Leukemia, 33, 1011-1022 (2019)), it was observed that BTZ-resistant MM1.S maintained its sensitivity to PDIA1 inhibition by CCF642-34. The resistant MM1.S cells had an LD50 of 60±11 nM compared to 118±21 nM for parental cells. (FIG. 3B,E). Interestingly, BTZ-resistant MM1.S cells were ~2-fold more sensitive to PDIA1 inhibition compared to parental BTZ-naïve MM1.S cells. This effect in BTZ-resistant MM1.S cells may be in part be due to increased dependence of resistant MM1.S cells on PDIA1, reflected in adaptive increase of PDIA1 (FIG. 5A,C,D).

Figure 5F:
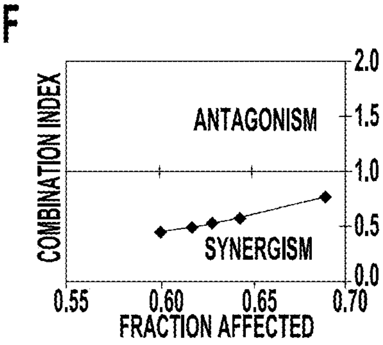
Figure 5G:
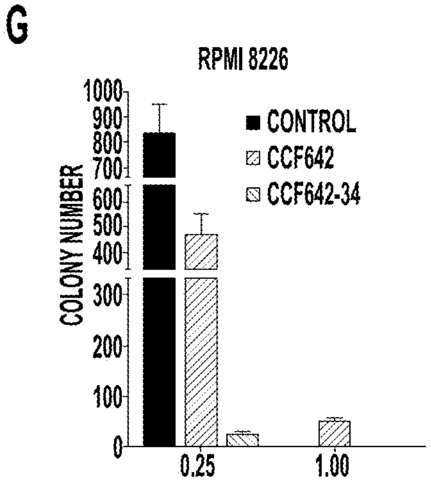
Figure 5H:
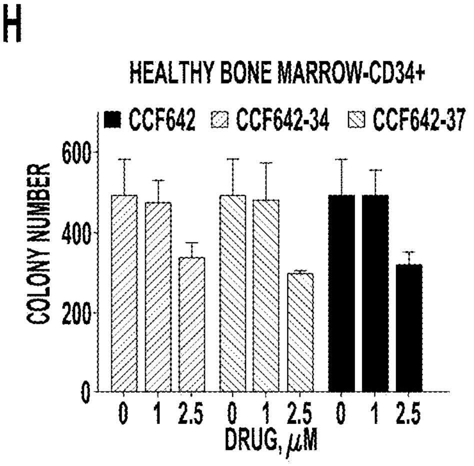

In addition, the inventors also examined if PDIA1 inhibition by CCF642-34 was synergistic or antagonistic to BTZ by Chou and Talalay assay. Chou, T.-C., Cancer Res., 70, 440-446 (2010) Combined treatment of MM1.S-luc with CCF642-34 and BTZ demonstrated a clear synergy in the low dose range, which disappeared with an increasing concentration of either drug due to pronounced cell death. For the lower dose range, which affected 70% of myeloma cells or less, a synergistic combination index (CI) below 1 was observed for PDIA1 inhibition combined with BTZ in treatment-naïve MM1.S cells (FIG. 5F). This synergy is likely explained by an increase in misfolded proteins upon inhibition of disulfide bond formation, leading to the greater dependence on proteasome to resolve ER stress. Ellgaard et al., Trends Biochem. Sci. 2018, 43, 32-43, Interestingly, CCF642-34 is 20-fold more potent in restricting the colony-forming abilities of MM cells, RPMI-8226, compared to its effect on the clonogenic potential of CD34+ HSPCs derived from healthy bone marrow, supporting PDIA1 as a target with favorable therapeutic index in multiple myeloma (FIG. 5G-H).

Figure 6A:
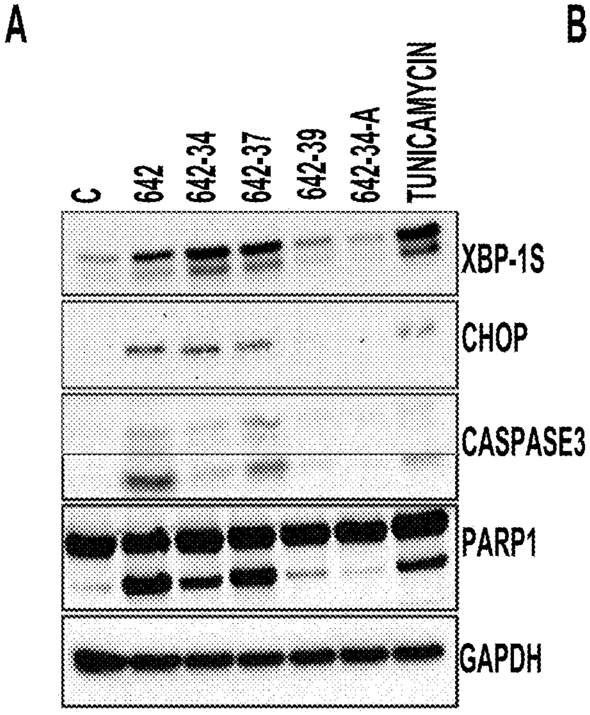
FIGS. 6A-6C provide graphs and images showing PDIA1 inhibition by CCF642 analogues induce acute endoplasmic reticulum (ER) stress response and lead to apoptosis. Multiple myeloma cells (MM1.S) were treated with 3 μM of CCF642, -34, -37, -39, -34-A, and Tunicamycin (as a control). The status of ER sensors (XBP-1S, IRE1α oligomerization, and induction of C/EBP homology protein (CHOP)) along with apoptosis markers (cleaved caspase 3 and PARP1) were monitored. (A) MM1.S cells were treated for 4 h with CCF642 and its indicated analogues. (B) MM1.S cells were treated with CCF642-34 in a time course. (C) MM1.S, MM1.S.luc, and BTZ-resistant MM1.S.luc cells were stained with the H2DCFDA ROS detection and then treated with 2.5 μM CCF642-34 up to 4 h.
Figure 6B:
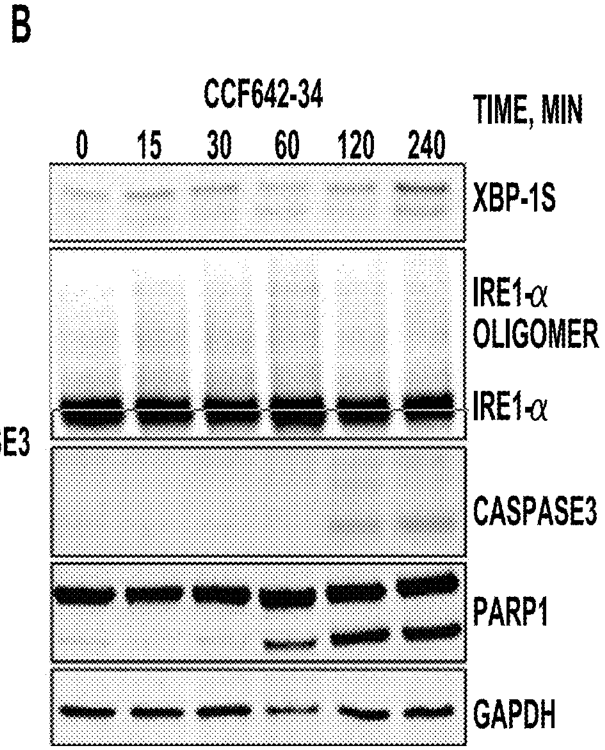
Figure 6C:
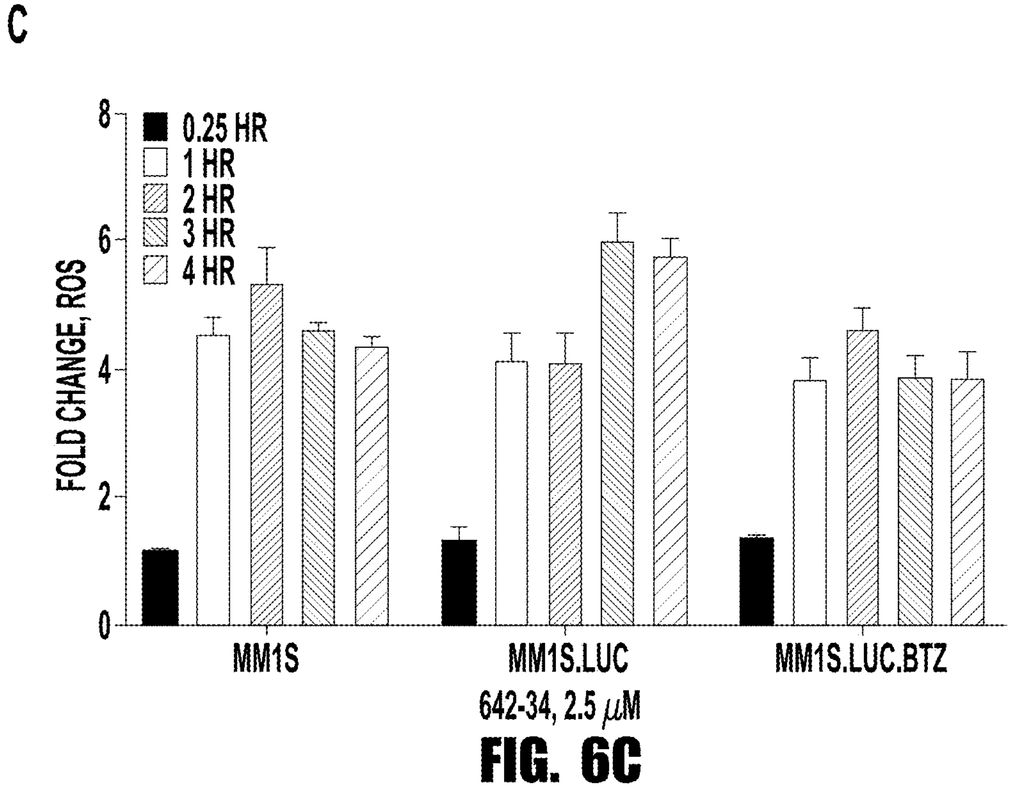

CCF642 Analogues Induce Acute ER Stress Response Followed by Apoptosis in MM1.S Cells To understand the mechanism of cell death induced by CCF642 analogues, the ER response and apoptosis were investigated. MM1.S cells were exposed to CCF642-34, CCF642-37, and also to the less effective analogue CCF642-39 as a control. While CCF642-34 and CCF642-37 induced a robust ER stress response, as evident from the induction of spliced X-Box Binding Protein-1S (XBP-1S) and C/EBP homologous protein (CHOP). The treatment of cells with inactive analogue CCF642-39 and CCF642-34A (FIG. 2) failed to induce acute ER stress response, consistent with their lack of PDIA1 inhibition (FIG. 6A). The induction of ER stress response is acute and leads to irreversible pro-apoptotic signaling as demonstrated by the extensive cleavage of PARP and caspase 3 (FIG. 6B). ER stress was observed after 15 min of exposure (expression of XBP-1S and IRE1a oligomerization) and lasted for several hours in the presence of the drug (FIG. 6B). The ER stress induced by PDI inhibition is irreversible and induces programmed cell death reflected in PARP and caspase 3 cleavage that starts ~1 h post-treatment (FIG. 6B). As expected with PDI inhibition and ER stress, treatment with CCF642-34 robustly increased reactive oxygen species (ROS) in myeloma cells, observable within 25 min and peaking between 2-3 h where 4-6-fold increase was detected by carboxy-H2DCFDA (FIG. 6C). As a result of increased ROS, upregulation of NRF2 pathway genes was observed.

Greater Selectivity of CCF642-34 for PDIA1 Inhibition Translates into a Narrower Band Gene Expression Profile than CCF642

Figure 7A:
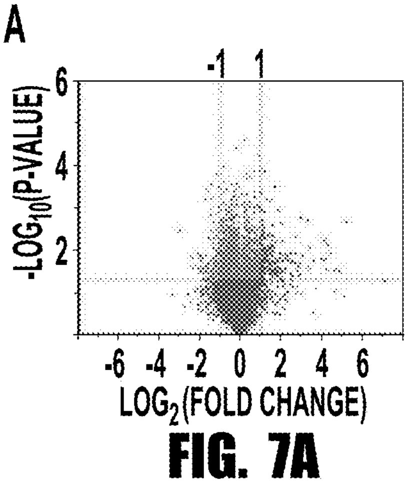
FIGS. 7A-7H provide graphs showing CCF642-34 is selective for PDIA1 inhibition-induced ER stress response pathway. MM1.S cells were treated with 3 μM of either CCF642 or CCF642-34 for 6 h, and gene expression analysis was performed by RNA sequencing. (A,B) Volcano plots showing CCF642-34 and CCF642 compared to DMSO control. The criteria for differential expression were at least a 2-fold change with p value less than 0.05. The analysis was performed in Originlab, Version 2019b (OriginLab Corporation, Northampton, MA, USA). (C) Differentially upregulated (red) and downregulated (green) genes between CCF642-34 and CCF642 were compared in Venn diagrams. The diagram was generated using a web-based bioinformatics server. (D,E) Hierarchical clusterings with heat map of MM1.S cells treated with vehicle CCF642-34 or CCF642 are shown for response to endoplasmic reticulum stress and unfolded protein response gene sets. (F-H) Heat maps of PERK and ATF6 target genes, Nrf2, and ER-associated degradation (ERAD) pathways are compared between control and inhibitor-treated MM1.S cells. Data analysis was performed using a web-based server and the Broad Institute Morpheus software.
Figure 7B:
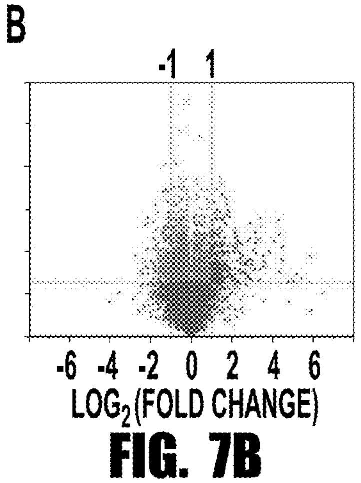
Figure 7C:
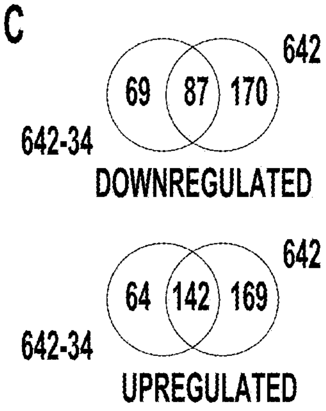
Figure 7F:
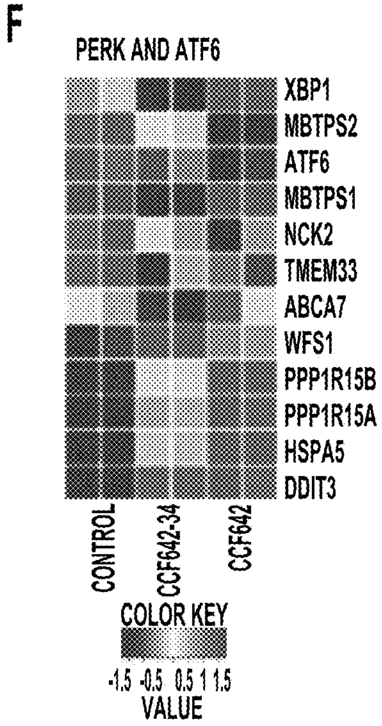
Figure 7D:
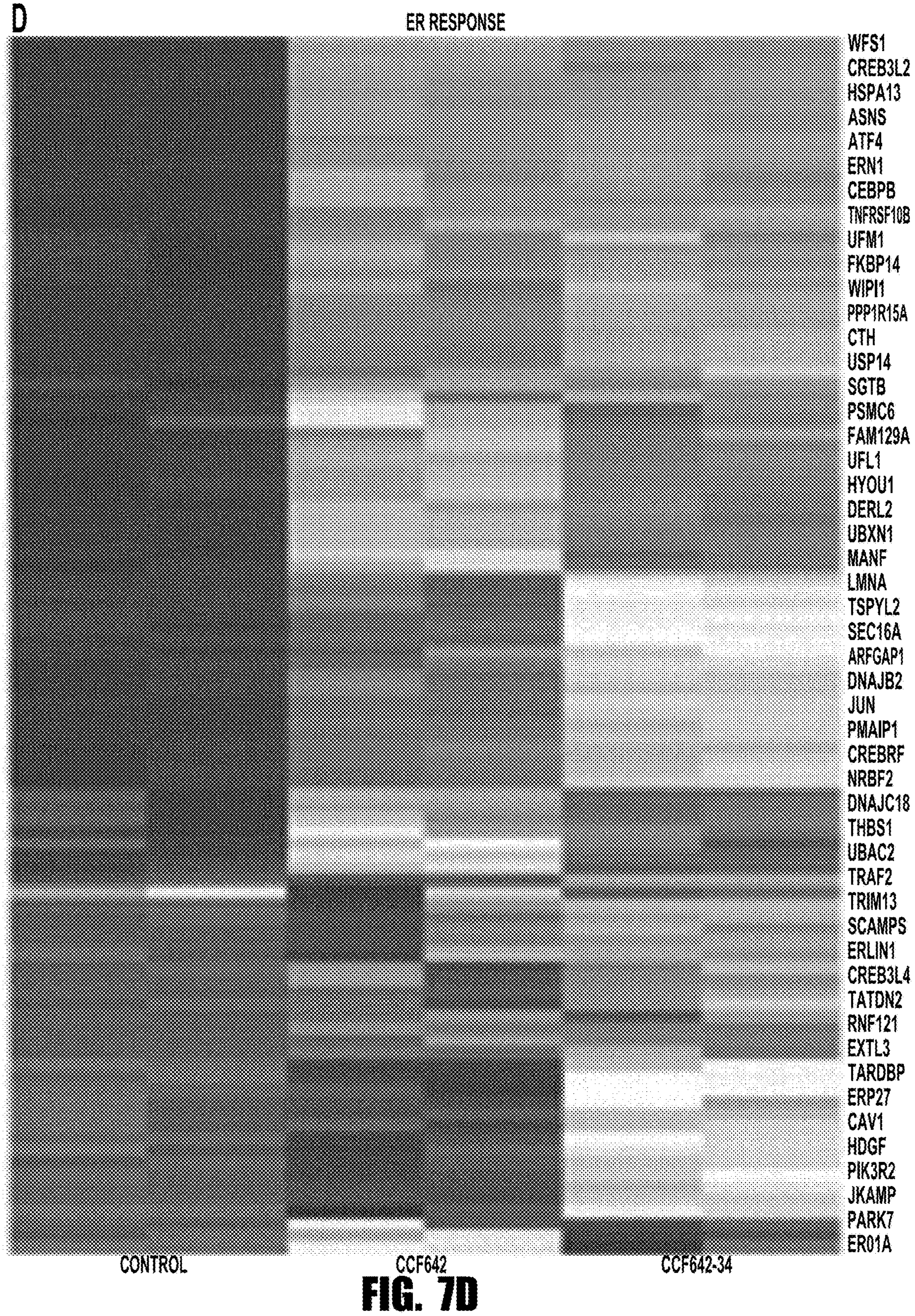
Figure 7E:
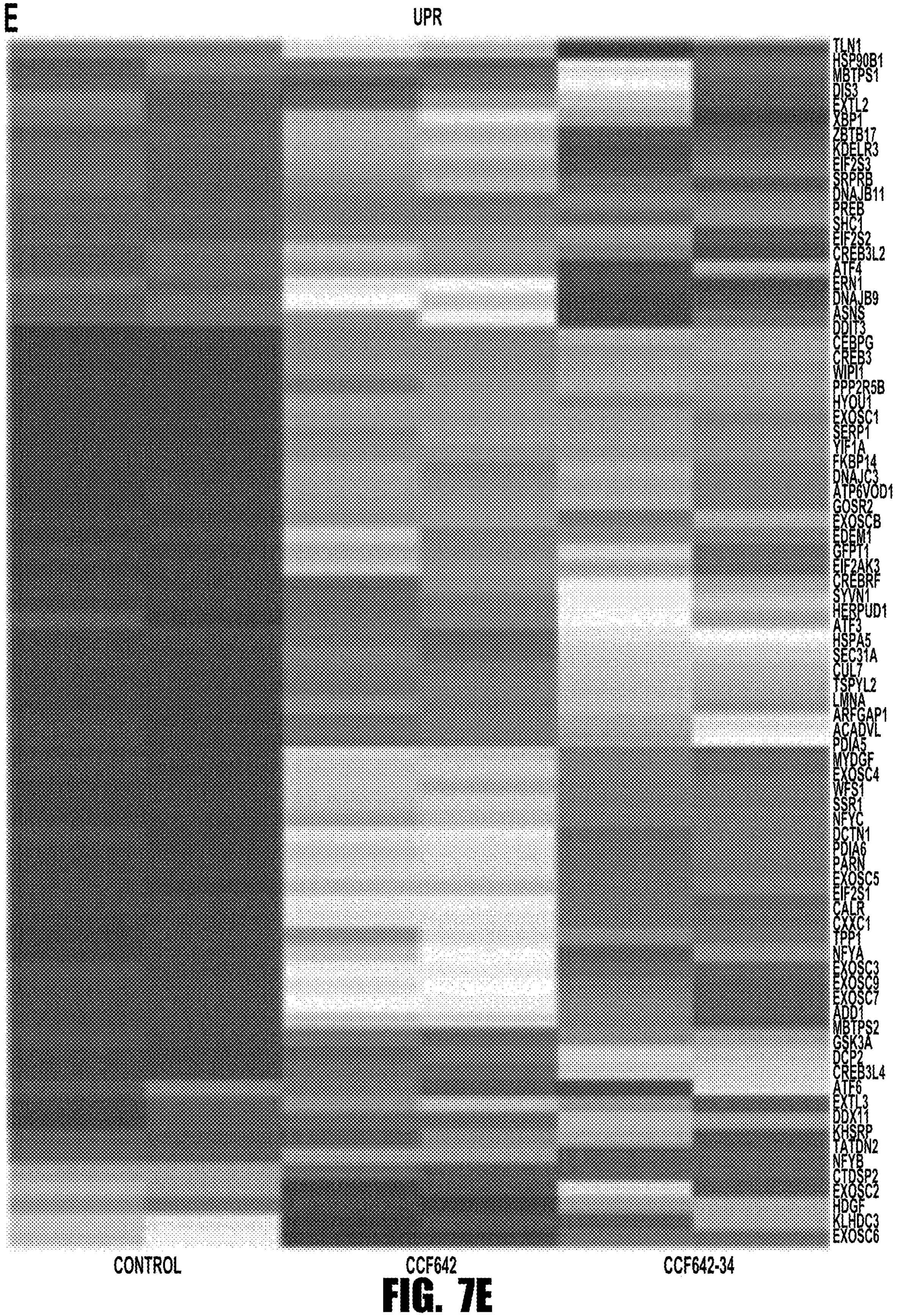
Figure 7G:
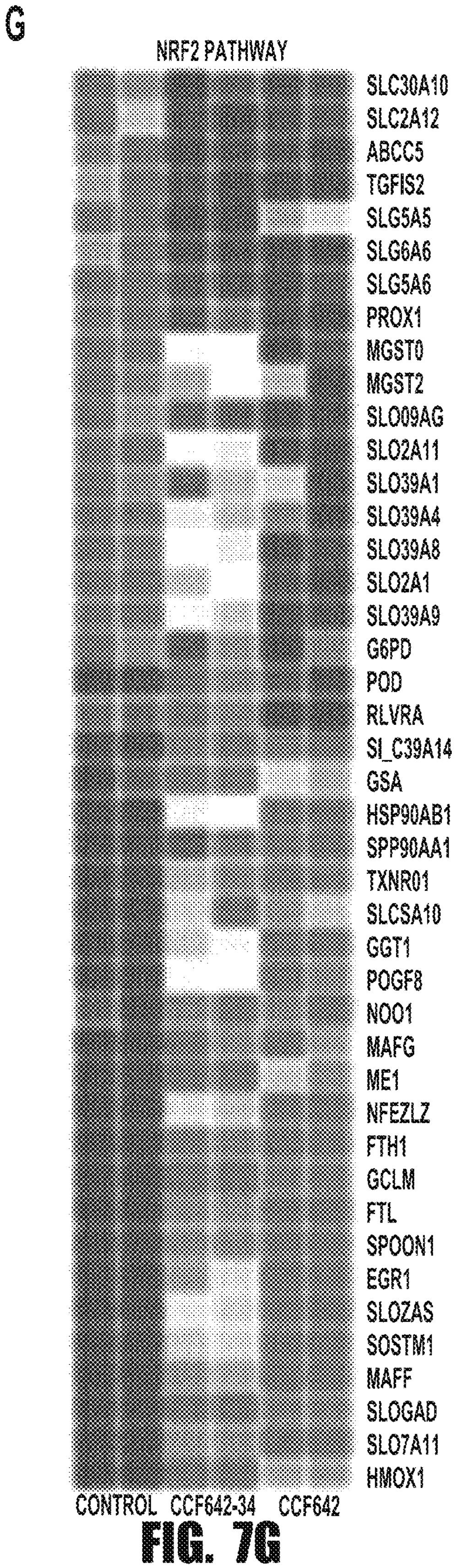
Figure 7H:
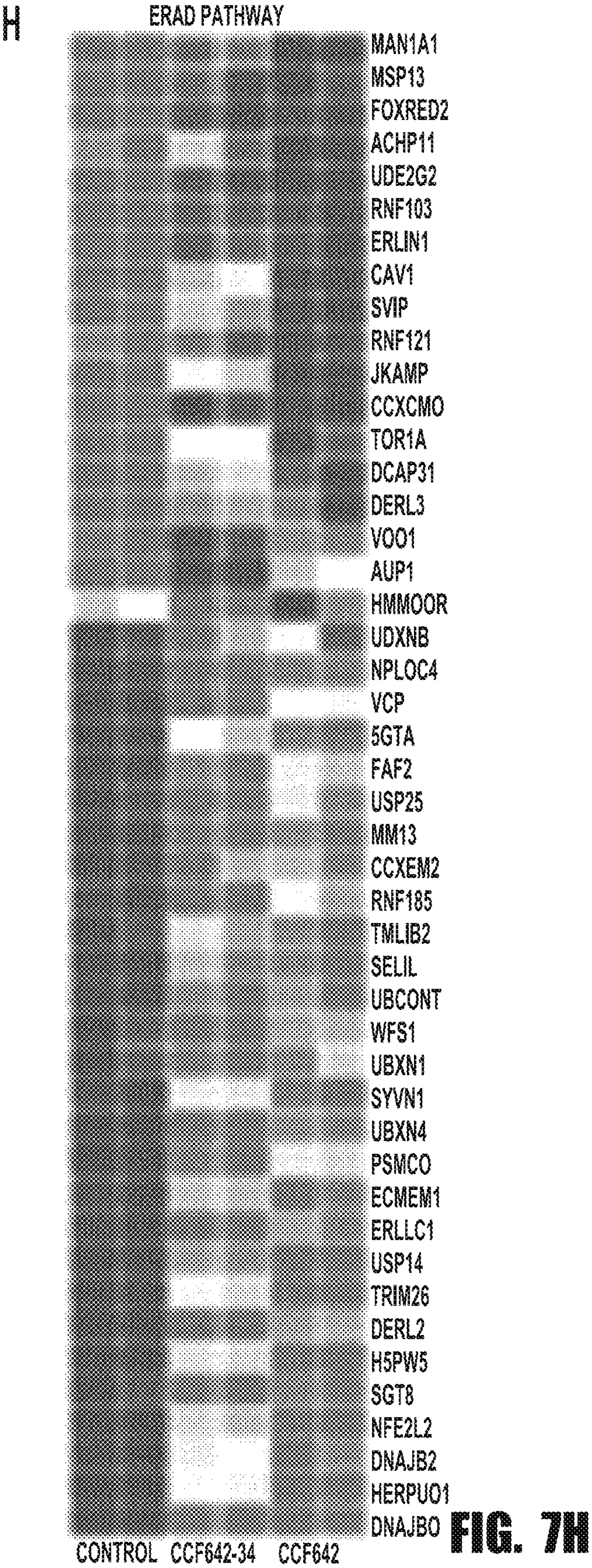

To investigate whether CCF642-34 affects gene expression changes that can be differentiated from CCF642, transcriptomic profiling of MM1.S cells treated with either of these two compounds at 3 μM for 6 h or vehicle control was performed using whole exome mRNA sequencing. Volcano plots were used to visualize differential expression (2-fold change with p value less than 0.05). Treatment of MM1.S cells with CCF642-34 or CCF642 changed the expression of 362 and 568 genes, respectively, compared to vehicle control (FIG. 7A,B). Among these differentially expressed genes, 87 downregulated and 142 upregulated genes were common to both compounds, including downregulation of cell division and mitotic cell cycle processes and upregulation of response to ER stress, unfolded protein response, and apoptotic gene sets (FIGS. 2, 5D-H). CCF642-34 treatment resulted in the down- and upregulation of 156 and 206 genes, whereas CCF642 caused down- and upregulation of 257 and 311 genes, respectively (FIG. 7C). Hierarchical clustering showed distinct gene expression profiles in 642-34- and 642-treated MM1.S cells and a narrower spectrum of genes involved in response to ER stress and UPR that was affected in expression after CCF642-34 compared to CCF642 treatment in MM1.S cells (FIG. 7D,E). Consistent with the acute ER stress, a further gene set enrichment analysis suggested upregulation of more than half of the ER-associated PERK and ATF6 target genes expression after 6 h of CCF642-34 treatment (FIGS. 2, 7F). In addition, genes associated with ubiquitin catabolism were also upregulated, a sign of the induction of unresolvable acute ER stress response caused by the accumulation of unfolded proteins. For example, the positive early sensor of ER stress response gene TRIB3 (Tribbles homolog 3), a negative regulator of NFkB that induces TRAIL and TNF activation-associated cell death (Eyers et al., Trends Cell Biol., 27, 284-298 (2017)), was nearly 20-fold upregulated compared to controls (FIG. 2).

Figure 8A:
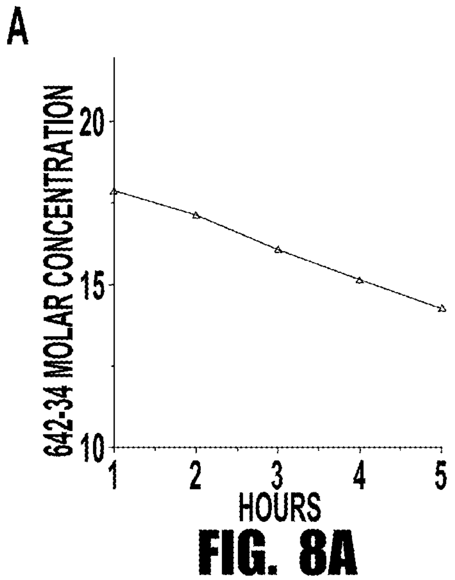
FIGS. 8A & 8B provide graphs showing the stability of CCF642-34 and restriction of multiple myeloma in a syngeneic mouse model by PDIA1-inhibitor CCF642-34. (A) The stability of CCF642-34 was measured against oxidative metabolism by human liver microsomes. CCF642-34 (20 μM) was incubated with 0.25 mg/mL of human liver microsomes for 5 h. The residual compound at indicated time points was measured by HPLC (Agilent 1260 Infinity II) interfaced with reverse phase C18 column using 280 nm and 245 nm detection wavelength. The standard curve of known concentrations of CCF642-34 was obtained from the area under the peak at two wavelengths, and the remaining CCF642-34 was estimated. Data are representative of two independent experiments. (B) 5TGM1-luc/C57BL/KaLwRij mouse models of myeloma (3 males, 3 females per treatment group) were engrafted with $2\times10^6$ 5TGM1-luc cells via tail vein injection and treated 3 times a week for 8 weeks per oral gavage with 20 mg/kg of CCF642-34 dissolved in 10% 2-hydroxy-propyl-o-cyclodextrin. The survival of each group was monitored, and Kaplan-Meier survival analysis was performed. All control animals required euthanasia before 52 days (due to paraparesis, weight loss, poor general condition), while 3 out of 6 mice treated with CCF642-34 lived beyond 6 months with no sign of disease.

CCF642-34 is Pharmacologically Stable to Acid Exposure and does not Undergo Rapid Hepatic Metabolism To evaluate pharmacological properties of CCF642-34, the stability in acidic conditions (6 N HCl) and upon exposure to human liver microsomes was tested. After exposure to acid for 3 h, greater than 80% of CCF642-34 could be recovered and the half-life in human liver microsomes was greater than 5 h, suggesting it would remain intact during gastric passage and not undergo substantial first-pass elimination (FIG. 8A). Incubation with HCl or human liver microsome did not compromise the specific activity of CCF642-34. It was therefore concluded that CCF642-34 may be orally bioavailable and effective against MM in vivo.

Figure 8B:
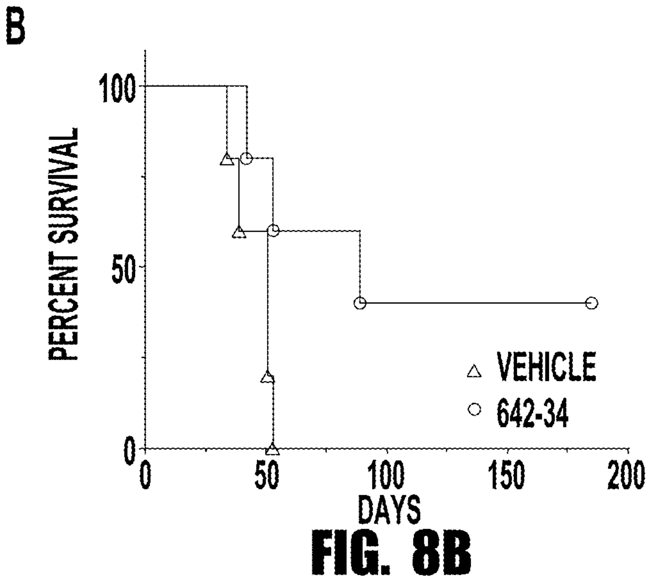

CCF642-34 Prolonged Survival of Mice in the 5TGM1 Syngeneic Mouse Model of Myeloma To evaluate whether CCF642-34 achieved anti-myeloma efficacy after oral administration in vivo we used the 5TGM1-luc/C57BL/KaLwRij syngeneic mouse model. Two million 5TGM1-luc myeloma cells were injected by tail vein, and a week later treatment started with vehicle (10% 2-hydroxy-propyl-o-cyclodextrin w/v in water) or CCF642-34 dissolved in vehicle given by oral gavage 3 times a week for 8 weeks. Mouse weight was monitored along with systemic symptoms of distress or disease. According to IACUC protocol guidelines, a drop of 20% in body weight, paraparesis, or behavioral signs of distress constituted experimental endpoints and mandated euthanasia. All vehicle control animals required euthanasia or expired by 52 days, while 3 out of 6 CCF642-34-treated mice lived beyond 180 days with no sign of disease (FIG. 8B). The intensity of luminescence was not good enough for the detection of bioluminescence, which is a common issue in the imaging of B57 black 6 mice. Therefore, the inventors primarily monitored the survival, and the disease burden was determined in the bone marrow cells at the time of sacrifice of a moribund mice. The survival data were significant according to the Mantel-Cox test (p=0.0391). Treatment caused no obvious adverse events as assessed by weight and animal behavior (data not shown). Results confirmed oral bioavailability and in vivo efficacy of CCF642-34 against myeloma.

Discussion

High baseline ER stress with an unfolded protein response (UPR) operating at capacity to prevent cell death is the result of high protein synthesis and secretion rate in neoplastic plasma cells that face micro-environmental stressors, which further increase the misfolded protein load. Protein homeostasis is central to the survival of highly proliferative malignant cells in general and MM cells in particular, which explains the efficacy of proteasome inhibition in the treatment of MM. As an incurable disease for the overwhelming majority of patients, with resistance developing to proteasome inhibitors and other novel drugs including CD38 antibodies, the treatment-refractory state of myeloma portends short survival below 6 months and represents an unmet medical need. The inventors found that patients with relapsed or refractory disease who expressed higher levels of PDIA1, the bottleneck enzyme for folding secreted proteins that contain intramolecular disulfide bonds, have inferior survival. These observations suggested that targeting PDIA1 could be an effective treatment strategy. The PDIA1 inhibition not only targets the overburdened protein synthesis of myeloma, but may also help overcome the treatment-refractory state of proteasome inhibitors. Building on the small molecule scaffold that inactivates PDIA1 by covalent attachment to lysine adjacent to its active site (Vatolin et al., Ibid), the inventors developed a pharmacologically improved analogue with greater solubility, selectivity, potency, and oral bioavailability that may serve as a lead for clinical translation.

Previously, the inventors reported CCF642, a candidate small molecule PDI inhibitor with sub-micromolar IC50 with excellent safety in vitro and in vivo. Vatolin et al., Ibid. However, poor solubility and bioavailability were major hurdles for its clinical translation. Using a structure-guided medicinal chemistry approach, the inventors have significantly improved the solubility and in vitro efficacy as determined by the PDI inactivation constant $K_{inact}$. This improvement in the potency was also reflected in the selectivity of the compound for PDIA1. The whole cell approach used for evaluating the selectivity of CCF642-34 demonstrated highly preferential binding to PDIA1 without substantial off-target binding at nearly 60-fold above therapeutic (LD50) doses. CCF642-34 avoided off-target binding of CCF642 and affected the expression of a lower number of genes than CCF642 (FIG. 7). It proved more potent against myeloma cells than its parent, the less PDIA1-selective compound CCF642 (FIG. 5), and similarly induced the acute ER stress response that overwhelmed the capacity of myeloma cells to maintain proteostasis, hence leading to cell death (FIG. 6). Consistent with the accumulation of misfolded proteins caused by inhibition of the ER resident PDIA1 enzyme, CCF642-34 treatment induced all three arms of ER stress response pathways. Bhattarai et al., Trends Cell Biol., 30, 672-675 (2020) Noticeably, the cleavage of XBP1 generating XBP1s as a result of IRE1 activation was seen as early as 15 min after treatment, consistent with an increase of misfolded proteins in the ER. The PERK-induced ATF4-associated target gene along with ATF6 target genes were significantly upregulated in the treatment group compared to vehicle, further supporting that inhibition of PDIA1 by CCF642-34 occurs in cells and leads to increase in misfolded ER proteins that are sensed by PERK (FIG. 7F).

The kinetics of proteostasis of the secreted proteins in normal cells are guided by slower demand and are largely error-free; however, the malignant plasma cells that operate at maximum capacity can decrease the folding yield or rate of folding. The ER resident chaperones in such high stress conditions are unable to prevent the generation of toxic unfolded species. Indeed, the misfolded proteins in the ER are observed in some disease states that are known to program cell death, consistent with observations in MM cells. Either the ER increases its ability to handle misfolded proteins, or misfolded proteins are destroyed, or the cell goes to apoptosis. Radl et al., Am. J. Pathol., 132, 593-597 (1988). Dysregulation of unfolded protein response (UPR) and ER-associated degradation (ERAD) are exploited as MM cells' vulnerability by PDIA1 inhibition.

One of the most striking observations was that CCF642-34 was active against proteasome inhibitor-resistant cells. In the analysis of relapsed and refractory MM patients, either early (ERMM, 1-3 prior lines of treatment) or late (LRMM, >3 prior lines), the inventors observed an upregulation of PDIA1 expression, suggesting that the gain of ER function may contribute to the refractory state that results in poor survival. Most patients are treated upfront with proteasome inhibitors, and in the relapsed and refractory setting most have been exposed to two proteasome inhibitors. CCF642-34 had potent activity against myeloma cells that were made resistant to the proteasome inhibitor bortezomib (BTZ) through constant exposure, and a synergistic effect with bortezomib was observed in combination studies (FIG. 5). CCF642-34 was highly stable in human liver microsomes and upon exposure to acid. As expected, based on these characteristics it proved effective upon oral administration in a well-established syngeneic mouse model of myeloma. Radl et al., Ibid. The results are consistent with recent reports that found BTZ-resistant myeloma cells maintain sensitivity toward PDI inhibition. Robinson et al., Eur. J. Med. Chem., 186, 111906 (2020).

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A compound of formula I (I)

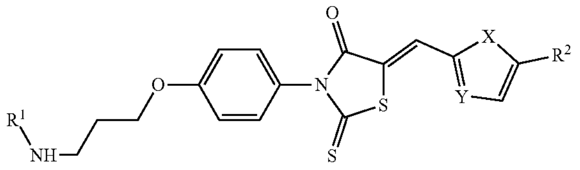

wherein:

$R^1$ is an amino acid or a modified amino acid linked to the compound through a peptide bond, $R^2$ is selected from CN, $SO_2CH_3$, $NO_2$, $CO_2R^3$, $CONHR^3$, $NH_2$, $NMe_2$ and $CF_3$, $R^3$ is selected from H or lower alkyl, X is O or S, and Y is C—H or N, or a pharmaceutically acceptable salt thereof.

2. The compound of claim 1, wherein $R^2$ is $NO_2$.

3. The compound of claim 1, wherein X is S and Y is C—H.

4. The compound of claim 1, wherein $R^1$ is tryptophan, phenylalanine, or tyrosine.

5. The compound of claim 1, wherein $R^1$ is tryptophan.

6. The compound of claim 1, wherein the compound has the structure:

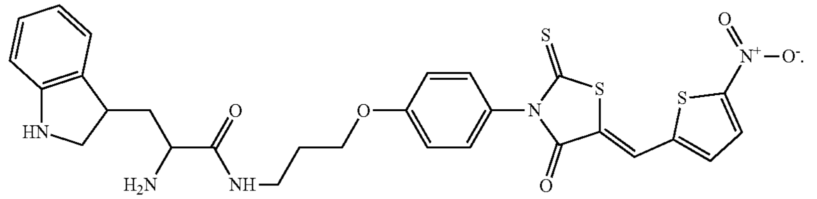

7. The compound of claim 1, wherein the compound is provided together with a pharmaceutically acceptable carrier.

* * * * *